United States Patent
Comee et al.

(10) Patent No.: US 12,161,291 B2
(45) Date of Patent: Dec. 10, 2024

(54) DEVICES, SYSTEMS, AND METHODS FOR ENDOSCOPE VALVE CONTROL

(71) Applicant: Boston Scientific Scimed, Inc., Maple Grove, MN (US)

(72) Inventors: Shaun D. Comee, Fiskdale, MA (US); Nathan T. Cummings, Worcester, MA (US); Paula R. Limberg, Northborough, MA (US); Brian Luis, Worcester, MA (US); Kyle P. Moore, Hopkinton, MA (US); Laura E. Richards, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 752 days.

(21) Appl. No.: 17/208,750

(22) Filed: Mar. 22, 2021

(65) Prior Publication Data

US 2021/0298569 A1 Sep. 30, 2021

Related U.S. Application Data

(60) Provisional application No. 62/994,019, filed on Mar. 24, 2020, provisional application No. 62/994,021, (Continued)

(51) Int. Cl.
*A61B 1/00* (2006.01)
*A61B 1/015* (2006.01)
(Continued)

(52) U.S. Cl.
CPC .......... *A61B 1/00068* (2013.01); *A61B 1/015* (2013.01); *A61B 1/12* (2013.01);
(Continued)

(58) Field of Classification Search
CPC ............ A61B 1/00082; A61B 1/00068; A61B 1/00094; A61B 1/015; A61B 1/126
See application file for complete search history.

(56) References Cited

U.S. PATENT DOCUMENTS

| 4,261,343 | A | * | 4/1981 | Ouchi | A61B 1/12 600/158 |
| 5,027,791 | A | * | 7/1991 | Takahashi | A61B 1/126 600/158 |
| 5,871,441 | A | * | 2/1999 | Ishiguro | A61B 1/122 600/159 |
| 6,346,075 | B1 | | 2/2002 | Arai et al. | |

(Continued)

FOREIGN PATENT DOCUMENTS

| EP | 2431062 A1 | 3/2012 |
| JP | 2000217777 A | 8/2000 |

(Continued)

OTHER PUBLICATIONS

International Search Report and Written Opinion for the International Patent Application No. PCT/US2021/023478, mailed Jun. 10, 2021, 49 pages.

(Continued)

*Primary Examiner* — Timothy J Neal
(74) *Attorney, Agent, or Firm* — Seager, Tufte & Wickhem, LLP

(57) ABSTRACT

Various embodiments are generally directed to devices, systems, and methods for controlling the flow of fluids in endoscopic systems, such as endoscopic ultrasound (EUS) enabled endoscopes. Some embodiments are particularly directed to valve sets and/or valve interface mechanisms for controlling air, water, and/or suction flow through a valve well for an endoscopic system. Several embodiments are directed to user interface mechanisms and techniques for enabling an operator to interact with and control endoscope valves. Many embodiments are directed to mechanisms and techniques for translating interface input motion into valve (Continued)

control motions. In one or more embodiments, the valve sets and/or valve interface mechanisms may be disposable.

15 Claims, 31 Drawing Sheets

Related U.S. Application Data filed on Mar. 24, 2020, provisional application No. 62/994,018, filed on Mar. 24, 2020, provisional application No. 62/994,015, filed on Mar. 24, 2020, provisional application No. 62/994,008, filed on Mar. 24, 2020, provisional application No. 62/994,024, filed on Mar. 24, 2020.

(51) Int. Cl.
  *A61B 1/12* (2006.01)
  *F16K 21/20* (2006.01)
  *A61B 1/018* (2006.01)

(52) U.S. Cl.
  CPC .......... *F16K 21/20* (2013.01); *A61B 1/00082* (2013.01); *A61B 1/018* (2013.01)

(56) References Cited

U.S. PATENT DOCUMENTS

| | | | |
|---|---|---|---|
| 2012/0088975 A1* | 4/2012 | Morimoto | A61B 1/00068 600/159 |
| 2019/0125167 A1 | 5/2019 | Taniguchi | |
| 2019/0350444 A1 | 11/2019 | Saiga | |

FOREIGN PATENT DOCUMENTS

| | | |
|---|---|---|
| JP | 2007111266 A | 5/2007 |
| WO | 2019225562 A1 | 11/2019 |

OTHER PUBLICATIONS

International Search Report and Written Opinion for the International Patent Application No. PCT/US2021/023479, mailed Jul. 9, 2021, 12 pages.
International Search Report and Written Opinion for the International Patent Application No. PCT/US2021/023482, mailed Jul. 9, 2021, 12 pages.
International Search Report and Written Opinion for the International Patent Application No. PCT/US2021/023484, mailed Jul. 9, 2021, 12 pages.

* cited by examiner

100

SUCTION VALVE ASSEMBLY 102

SUCTION VALVE WELL 104

SUCTION CHANNEL 106

WORKING CHANNEL 108

BALLOON CHANNEL 114

ATMOSPHERIC CHANNEL 116

SUCTION VALVE SET 118

WORKING CHANNEL VALVE 120

BALLOON VALVE 122

ATMOSPHERIC VALVE 124

VALVE INTERFACE MECHANISM 126

BIASING MEMBER SET 128

USER INTERFACE MECHANISM 130

AIR/WATER (AW) VALVE ASSEMBLY 202

AW VALVE SET 204

| AIR INPUT CHANNEL 206 | WATER INPUT CHANNEL 208 | AIR OUTPUT CHANNEL 210 |
|---|---|---|
| WATER OUTPUT CHANNEL 212 | BALLOON CHANNEL 214 | ATMOSPHERIC CHANNEL 216 |

AW VALVE SET 218

| PRIMARY CONTROL VALVE 220 | AIR INPUT VALVE 222 | ATMOSPHERIC VALVE 224 |
|---|---|---|

VALVE INTERFACE MECHANISM 226

| BIASING MEMBER SET 228 | USER INTERFACE MECHANISM 230 |
|---|---|

FIG. 2

DEVICES, SYSTEMS, AND METHODS FOR ENDOSCOPE VALVE CONTROL

PRIORITY

The present application claims the benefit of priority under 35 U.S.C. § 119 to U.S. Provisional Application Ser. Nos. 62/994,008, 62/994,015, 62/994,018, 62/994,019, 62/994,021, and 62/994,024, each filed Mar. 24, 2020, the disclosures of which are incorporated herein by reference in their entirety.

FIELD

The present disclosure relates generally to the field of medical devices. In particular, the present disclosure relates to devices, systems, and methods to control flow through a valve well for an endoscope.

BACKGROUND

An endoscopy procedure is used in medicine to access the interior of a body for diagnostic and/or therapeutic procedures. Oftentimes, the endoscopy procedure uses an endoscope to examine or manipulate the interior of a hollow organ or cavity of the body. Unlike many other medical imaging techniques, endoscopes are inserted directly into the organ. Typically, an endoscope includes one or more channels for the flow of one or more fluids therethrough. For example, one or more of suction, air, and water may flow through an endoscope. A valve assembly may be configured and used in various fashion to control the flow of the one or more fluids through the endoscope. In the case of an echoendoscope or ultrasound endoscope, control of fluids may also be used to inflate and deflate a balloon at the end of an endoscope.

It is with these considerations in mind that a variety of advantageous outcomes may be realized by the devices, systems and methods of the present disclosure.

SUMMARY

In one aspect, the present disclosure relates to a medical device comprising a valve set and a valve interface mechanism. The valve set may include a primary control valve, an air input valve, and an atmospheric valve. The primary control valve may be configured to control flow between a water input channel, a water output channel, and a balloon channel of a valve well. The air input valve configured to control flow through an air input channel of the valve well. The atmospheric valve may be configured to control flow through an atmospheric channel. The valve interface mechanism may include a set of one or more biasing members and a user interface mechanism. The one or more biasing members may comprise first, second, and third biasing members, the user interface mechanism may be operable between a first state, a second state, a third state, and a fourth state. The first state may comprise the valve set configured to place the air input channel in fluid communication with the atmospheric channel, the second state may comprise the valve set configured to place the air input channel in fluid communication with the air output channel, the third state may comprise the valve set configured to place the water input channel in fluid communication with the water output channel, and the fourth state may comprise the valve set configured to place the water input channel in fluid communication with the balloon channel. The first, second, and third biasing members may position the user interface mechanism in the first state when user input is absent. In some embodiments, the first biasing member prevents the atmospheric valve from blocking flow through the atmospheric channel when user input is absent. In various embodiments, the second biasing member prevents the air input valve from blocking flow through the air input channel when user input is absent. In many embodiments, the third biasing member positions the primary control valve to block flow between the water input channel and the water output channel when user input is absent. In several embodiments, the third biasing member positions the primary control valve to block flow between the water input channel and the balloon channel when user input is absent. In one or more embodiments, the first biasing member may comprise a pressure differential between a portion of the atmospheric valve and the atmospheric channel created by configuring the valve set to place the air input channel in fluid communication with the atmospheric channel. In various embodiments, the user interface mechanism may comprise an interface, a hat including at least a portion of the air input valve, and one or more linkages, wherein a first linkage is coupled to the primary control valve. In some such embodiments, the first biasing member couples the first linkage to the interface. In many such embodiments, the second biasing member couples the first linkage to the hat. In several such embodiments, the third biasing member couples the hat to a second linkage coupled to the valve well. In various embodiments, the hat may comprise at least a portion of the air input valve. In some embodiments, the first biasing member may comprise a first bellow and the second biasing member comprising a second bellow, wherein the first and second bellows are disposed in series between the air input valve and the atmospheric channel. In some such embodiments, the first and second bellows provide different biasing forces. In various embodiments, the atmospheric valve is biased open due to pressure created by flow from the air input channel. In several embodiments, the valve set includes a flapper valve configured to open due to a pressure buildup when the atmospheric valve blocks flow through the atmospheric channel and the air input valve permits flow through the air input channel.

In another aspect, the present disclosure relates to a method. The method may include placing an air input channel of a valve well in fluid communication with an atmospheric channel based on operation of a valve interface mechanism to a first state, the valve set comprising a primary control valve, an air input valve, and an atmospheric valve, wherein the primary control valve comprises the air input valve. The method may include placing the air input channel in fluid communication with an air output channel of the valve well based on operation of the valve interface mechanism to a second state. The method may include placing the water input channel in fluid communication with a water output channel of the valve well based on operation of the valve interface mechanism to a third state. The method may include placing the water input channel in fluid communication with the balloon channel of the valve well based on operation of the valve interface mechanism to a fourth state. In some embodiments, the method may include rotating an interface member in a first direction to operate the user interface mechanism to the second state and rotating the interface member in a second direction to operate the user interface mechanism to the third state and/or fourth state. In many embodiments, the method may include rotating the interface member adjust one or more valves in an air/water valve set via a cam. In several embodiments, the method may include operating one or more of a lever, a rocker switch, and an interface member to adjust between one or more of the first state, the second state, the third state, and the fourth state.

In still another aspect, the present disclosure relates to a method. The method may include configuring a valve set to place an air input channel of a valve well in fluid communication with an atmospheric channel based on operation of a user interface mechanism to a first state. The method may include configuring the valve set to place the air input channel in fluid communication with an air output channel of the valve well based on operation of the user interface mechanism to a second state. The method may include configuring the valve set to place the water input channel in fluid communication with a water output channel of the valve well based on operation of the user interface mechanism to a third state. The method may include configuring the valve set to place the water input channel in fluid communication with the balloon channel of the valve well based on operation of the user interface mechanism to a fourth state. In some embodiments, the method may include configuring a first biasing member to compress when the atmospheric channel is sealed with the atmospheric valve. In various embodiments, the method may include configuring a second biasing member to compress when the air input channel is sealed with the air input valve. In many embodiments, the method may include configuring the second biasing member to compress when the water input channel is placed in fluid communication with the water output channel. In one or more embodiments, the method may include configuring a third biasing member to compress when the water input channel is placed in fluid communication with the balloon channel.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 1 includes a block diagram of an exemplary suction valve assembly, according to one or more embodiments described herein.

FIG. 2 includes a block diagram of an exemplary air/water (AW) valve assembly, according to one or more embodiments described herein.

DETAILED DESCRIPTION

Figure 3A:
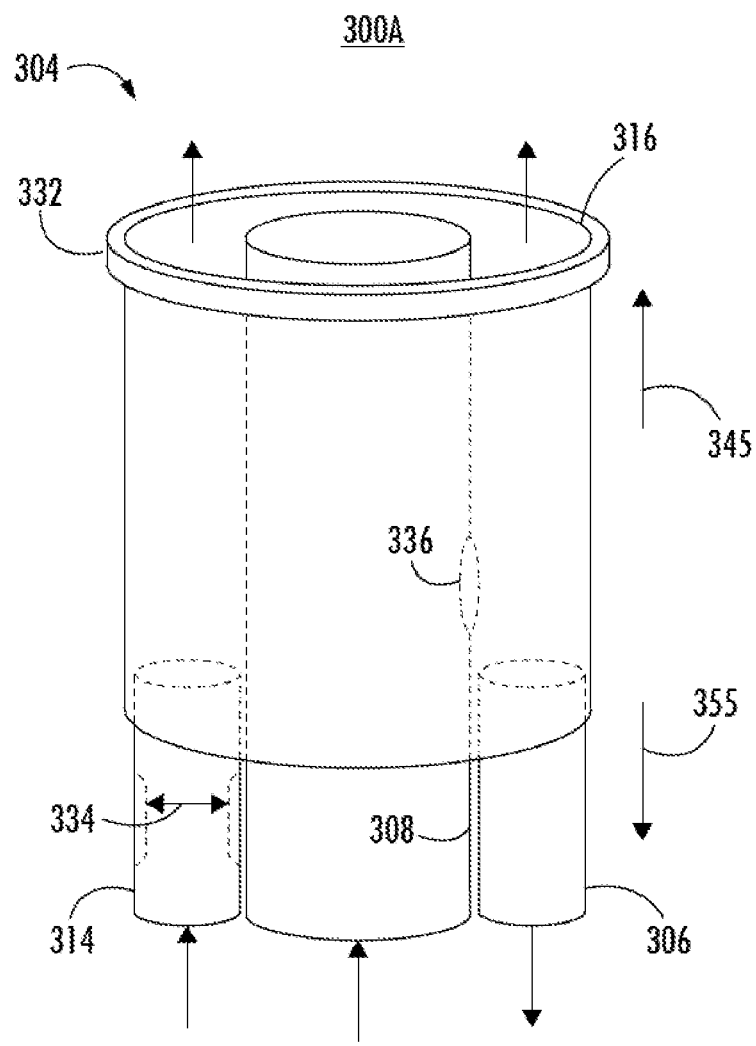
FIGS. 3A-3D illustrate various aspects of an exemplary suction valve well, according to one or more embodiments described herein.

Various embodiments are generally directed to devices, systems, and methods for controlling the flow of fluids in endoscopic systems, such as endoscopic ultrasound (EUS) enabled endoscopes. Some embodiments are particularly directed to valve sets and/or valve interface mechanisms for controlling air, water, and/or suction flow through a valve well for an endoscopic system. Several embodiments are directed to user interface mechanisms and techniques for enabling an operator to interact with and control endoscope valves. Many embodiments are directed to mechanisms and techniques for translating interface input motion into valve control motions. In one or more embodiments, the valve sets and/or valve interface mechanisms may be disposable. These and other embodiments are described and claimed.

Some challenges when controlling the flow of fluids through endoscopes include unreliable valves prone to failure. For example, many valves and valve interface mechanisms are fragile and likely to leak. These issues can be compounded when the components are designed, constructed, and/or assembled economically to facilitate disposal after a single use. Alternatively, these issues can be compounded when reusable components are worn down from multiple use/cleaning cycles. Adding further complexity, user interface mechanisms may be confusing to operate and require a steep learning curve. For instance, delicate and nonintuitive movements may be required to accurately control fluid flows. Further, little or no feedback may be provided to indicate how a set of valves is arranged. For example, an operator may not be able to easily discern via a user interface mechanism whether the set of valves is arranged to provide suction to a working channel or provide suction to a balloon channel. These and other factors may result in devices, systems, and methods for controlling the flow of fluids through endoscopes that are difficult to use, inaccurate, inefficient, and unreliable, resulting in limited applicability and/or uncertain outcomes. Such limitations can drastically reduce the dependability, ergonomics, and intuitiveness of flow control in endoscopes and procedures performed therewith, contributing to reduced usability, adverse outcomes, excess fatigue, and lost revenues.

Various embodiments described herein include one or more components of a valve assembly, such as valves and/or valve interface mechanisms, that provide reliable and intuitive control of fluid flow through endoscopes. In several embodiments, the components may provide reliable operation while providing sufficient value to be disposable (e.g., single-use). In many embodiments, the components may provide accurate and intuitive interfaces to improve operator experience. For example, embodiments may utilize one or more of up-and-down, forward-and-back, side-to-side, and rotational interfaces to provide ergonomic and intuitive control of fluid flows through endoscopes. Some such embodiments may include one or more interface members, such as push/pull switches, bellows, rotational switches, knobs, buttons, and toggle switches. In many embodiments, one or more of the components may provide/enable tactile feedback. For example, one or more components of the valve interface mechanism may provide tactile or haptic feedback to indicate how a set of valves is arranged (e.g., arranged to permit/block flows between various channels). In some examples, the force to operate a user interface mechanism may vary to indicate transitions between valve states. In various embodiments, tactile feedback may be produced as a result of different components of a valve assembly coming into contact, such as due to received input.

In various embodiments, one or more of the components may be designed to simplify manufacturability. For instance, the location of one or more biasing members may simplify component assembly. In these and other ways, components/techniques described here may improve operator experience, decrease learning curves, improve reliability, and/or decrease manufacturing complexity via realization of more efficient and valuable devices, systems, and methods for controlling the flow of fluids in endoscopic systems. In many embodiments, one or more of the advantageous features may result in several technical effects and advantages over conventional technology, including increased capabilities and improved adaptability.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to specific medical devices and systems (e.g., an endoscope), it should be appreciated that such medical devices and systems may be used in a variety of medical procedures which require navigating one or more accessory tools through ductal, luminal, or vascular anatomies, including, for example, interventional radiology procedures, balloon angioplasty procedures, thrombolysis procedures, angiography procedures, Endoscopic Retrograde Cholangio-Pancreatography (ERCP) procedures, and the like. The disclosed medical devices and systems may be inserted via different access points and approaches, e.g., percutaneously, endoscopically, laparoscopically or some combination thereof.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, the term "distal" refers to the end farthest away from the medical professional/operator when introducing a device into a patient, while the term "proximal" refers to the end closest to the medical professional when introducing a device into a patient.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIGS. 1 and 2 illustrate block diagrams of exemplary valve assemblies in environments 100, 200, according to one or more embodiments described herein. In some embodiments, one or more components of environment 100 and/or environment 200 may be the same or similar to one or more other components described herein. Environment 100 may include a suction valve assembly 102 with a suction valve well 104, a suction valve set 118, and a valve interface mechanism 126. Environment 200 may include an air/water (AW) valve assembly 202 with an AW valve well 204, an AW valve set 218, and a valve interface mechanism 226. In one or more embodiments described herein, various components of suction valve assembly 102 and/or AW valve assembly 202 may interoperate to provide reliable and intuitive control of fluid flow through endoscopic systems. For example, one or more components of valve sets 118, 218 and valve interface mechanisms 126, 226 may provide reliable and intuitive control of fluid flow through suction valve well 104 or AW valve well 204. In many embodiments, components of a valve assembly may be classified as, belong to, include, implement, and/or interoperate with one or more of a valve well, a valve set, and a valve interface mechanism. For instance, a valve interface mechanism may include one or more portions of a valve. Embodiments are not limited in this context.

In environment 100, the suction valve well 104 may include suction channel 106, working channel 108, balloon channel 114, and atmospheric channel 116; the suction valve set 118 may include working channel valve 120, balloon valve 122, and atmospheric valve 124; and the valve interface mechanism 126 may include biasing member set 128 and user interface mechanism 130. In various embodiments, the channels of the suction well 104 may be connected to other components in an endoscopic system, such as via tubing or piping. In one or more embodiments described herein, the suction channel 106 may be connected to a suction source, the working channel 108 may be connected to a working channel of an endoscopic device (e.g., endoscope or component disposed therethrough), the balloon channel 114 may be connected to a balloon of an endoscopic device. In several embodiments, suction valve set 118 and valve interface mechanism 126 may control the flow of suction (e.g., induced by negative pressure relative to atmospheric pressure) through suction valve well 104. In several such embodiments, the flow of suction may be controlled to the suction channel 106 from one of the working channel 108, the balloon channel 114, and the atmospheric channel 116.

In environment 200, the AW valve well 204 may include air input channel 206, water input channel 208, air output channel 210, water output channel 212, balloon channel 214, and atmospheric channel 216; the AW valve set 218 may include primary control valve 220, air input valve 222, and atmospheric valve 224; and the valve interface mechanism 226 may include biasing member set 228 and user interface mechanism 230. In various embodiments, the channels of the AW well 204 may be connected to other components in an endoscopic system, such as via tubing or piping. In one or more embodiments described herein, the air input channel 206 may be connected to a pressurized air source, the water input channel 208 may be connected to a water source, the air output channel 210 may be connected to an air channel of an endoscopic device (e.g., endoscope or component disposed therethrough), the water output channel 212 may be connected to a water channel of an endoscopic device, and the balloon channel 214 may be connected to a balloon of an endoscopic device. In several embodiments, AW valve set 218 and valve interface mechanism 226 may control the flow of air and water through AW valve well 204. In several such embodiments, the flow of air may be controlled from air input channel 206 to one of the air output channel 210, the atmospheric channel 216, or blocked, and/or the flow of water may be controlled from water input channel 208 to one of water output channel 212, the balloon channel 214, or blocked.

In many embodiments, suction valve assembly 102 and/or AW valve assembly 202 may be used in conjunction with an endoscopic system, such as an EUS system. In various embodiments, reference to a balloon may refer to a balloon in the EUS system that can be inflated/deflated to provide medium to facilitate transmission of sound waves and capturing of ultrasound images. For example, valve interface mechanism 126 may receive input to control the flow through suction valve well 104 to deflate the balloon by arranging the suction valve set 118 to place the suction channel 106 in fluid communication with the balloon channel 114. In another example, valve interface mechanism 226 may receive input to control the flow of water through AW valve well to inflate the balloon by arranging the AW valve set 218 to place the water input channel 208 in fluid communication with balloon channel 214. In other embodiments, one or more of the components of the valve assembly for AW and/or suction may be implemented in configurations that do not require or include a balloon, such as video capable scope with ultrasound functionality.

More generally, in several embodiments, each channel in a valve well may refer to a flow path comprising an input/output of a fluid from/to a corresponding entity. For example, suction channel 106 may refer to a flow path comprising an input from a suction source. In another example, an atmospheric channel may refer to a flow path comprising an output to the atmosphere. These and other aspects of the present disclosure will be described in more detail below, such as with respect to FIGS. 3A-4E. In various embodiments, each valve in a valve set may refer to a component that physically controls flow through or between one or more channels. For instance, when closed, the atmospheric valve 124 may block the flow of air out of the atmospheric channel 116. In another instance, in a first position, or first state, the primary control valve 220 may place the water input channel 208 in fluid communication with the water output channel 212, and in a second position, the primary control valve 220 may place the water input channel 208 in fluid communication with the balloon channel 214. These and other aspects of the present disclosure will be described in more detail below, such as with respect to FIGS. 5-12C.

In various embodiments, the valve interface mechanisms may include one or more components to enable control over the arrangement of valves in a valve set. In such embodiments, biasing member sets may include one or more, torsional springs, lever springs, coil spring, baffles, dampers, clips, and the like that provide a force to bias one or more components in a specific direction or position. For example, the biasing member set 228 may cause air to flow out the atmospheric channel when no input is being received. In an additional, or alternative example, the biasing member set 128 may provide differing resistance to operation of the user interface mechanism 130 between different states, such as to provide tactile indications of the state. In various embodiments, each of the user interface mechanisms 130, 230 may include one or more of an interface, an interface member, a user interface, a housing, a linkage, a knob, a lever, a rocker switch, a push/pull switch, a knob, a button, a diaphragm switch, a toggle switch, and the like. In some embodiments, an interface, an interface member, and/or a user interface may be the same or similar.

In several embodiments, user interface mechanisms may include one or more components to receive input and/or implement valve arrangements. For example, user interface mechanism 130 may include a user interface comprising a lever and one or more linkages to translate motion of the lever into appropriate motion of one or more valves to achieve a desired flow. In various embodiments, user interface mechanisms may include one or more biasing members and/or biasing members may include one or more user interface mechanisms. It will be appreciated that one or more components described herein in the context of a suction valve assembly may be utilized in or adapted for use in an AW valve assembly, and vice versa, without departing from the scope of this disclosure. For example, a rotational user interface mechanism described with respect to a suction valve interface mechanism may be utilized in or adapted for use in an AW valve interface mechanism. These and other aspects of the present disclosure will be described in more detail below.

FIGS. 3A-4E illustrate various aspects of exemplary valve well block diagrams of exemplary valve assemblies in environments 300A-D, 400A-E, according to one or more embodiments described herein. In some embodiments, one or more components of FIGS. 3A-4E may be the same or similar to one or more other components described herein. Environments 300A-D illustrate a suction valve well 304 comprising a suction channel 306, a working channel 308, a balloon channel 314 and an atmospheric channel 315. Environments 400A-E illustrate an AW valve well 404 with an air input channel 406, a water input channel 408, an air output channel 210, a water output channel 212, a balloon channel 214, and an atmospheric channel 216. In one or more embodiments described herein, fluid may flow through the valve wells based on the arrangement of one or more valves as positioned by one or more valve interface mechanisms. Embodiments are not limited in this context.

Referring to FIG. 3A, environment 300A illustrates various components of suction valve well 304. The suction valve well 304 may include a top 345 and a bottom 335. The suction channel 306, working channel 308, and balloon channel 314 may comprise respective entrances/exits towards the bottom 355 while the atmospheric channel 316 may comprise an entrance towards the top 345. In the illustrated embodiment, the balloon channel 314 includes a necking portion 334, the working channel 308 includes a well radial hole 336, and the atmospheric channel 316 includes a lip 332. In one or more embodiments, the necking portion 334 may enable a valve to prevent fluid flow through the balloon channel 314, such as by blocking the necking portion 334. In various embodiments, the well radial hole 336 may enable the working channel 308 to be placed in fluid communication with the suction channel 306. In several embodiments, the lip 332 may enable one or more suction valve sets and/or valve interface mechanisms to couple to the suction valve well 304. In many embodiments, valves and/or valve interface mechanisms may be inserted through atmospheric channel 316 for assembly of a suction valve assembly. It will be appreciated that the orientation and/or arrangement of one or more of the channels and/or flows may be modified in various embodiments without departing from the scope of this disclosure.

Figure 3B:
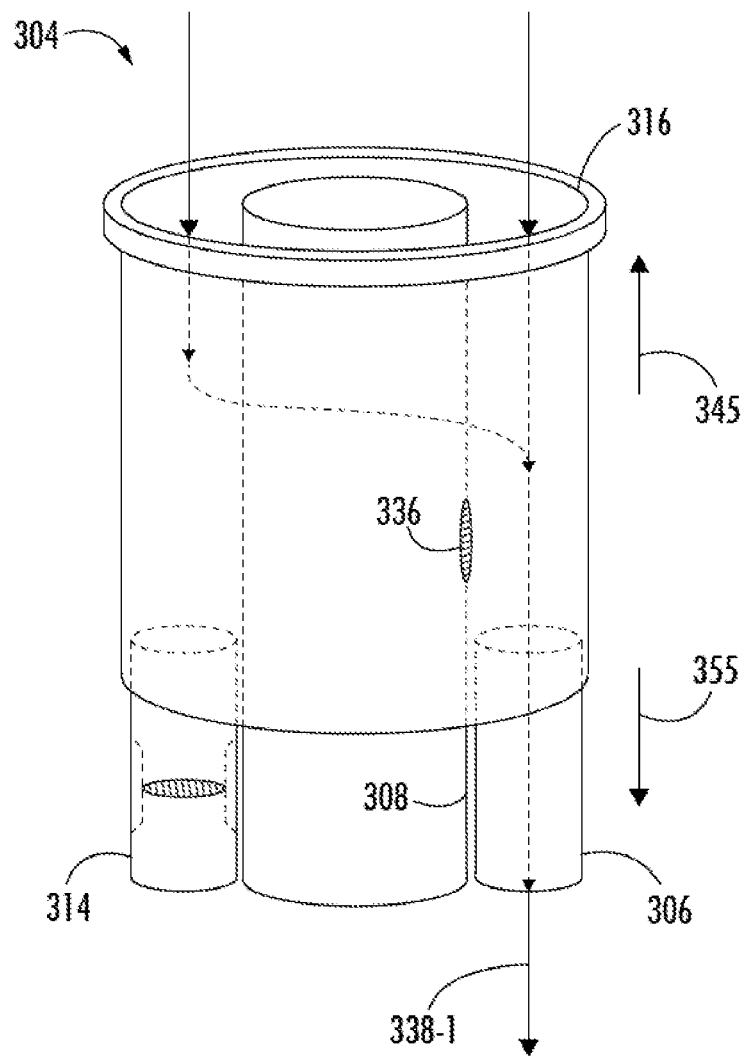

Referring to FIG. 3B, environment 300B illustrates a flow 338-1 through the suction valve well 304 in an atmospheric suction state 305-1. In the atmospheric suction state 305-1, flow 338-1 may enter via the atmospheric channel 316 and exit through the suction channel 306. For example, suction channel 306 may be an input in the handle of a medical scope that is connected to a vacuum system, such as for a hospital, home, and/or mobile device.

Further, in some embodiments, flow may be blocked through the balloon channel 314 at the necking portion 334 and flow may be blocked through the working channel 308 at the well radial hole 336. As will be discussed in more detail below, in operation, fluid communication with the atmosphere may be provided through a passage/channel in, or created by, one or more components (e.g., a valve inserted into the atmospheric channel 316). Further, one or more components may be used to seal portions of the atmospheric channel 316 to facilitate blocking of fluid communication with the atmosphere by an atmospheric valve.

Figure 3C:
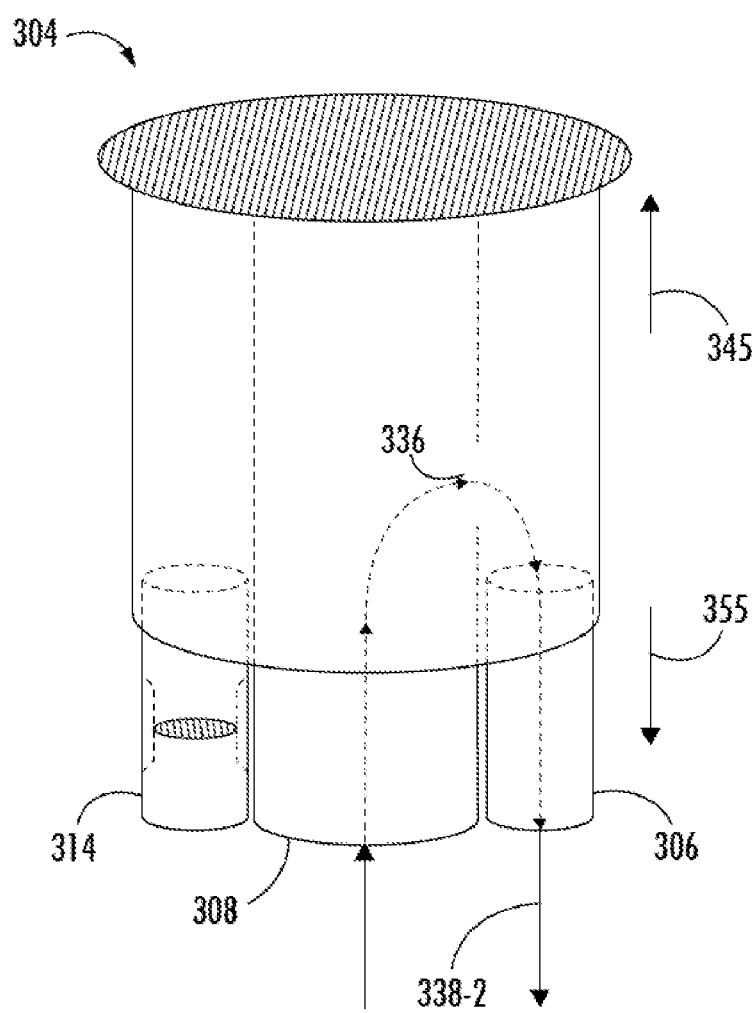

Referring to FIG. 3C, environment 300C illustrates a flow 338-2 through the suction valve well 304 in a working channel suction state 305-2. In the working channel suction state 305-2, flow 338-2 may enter via the working channel 308, pass through the well radial hole 336, and exit through the suction channel 306. Further, in many embodiments, flow may be blocked through the balloon channel 314 at the necking portion 334 and flow may be blocked through the atmospheric channel 316.

Figure 3D:
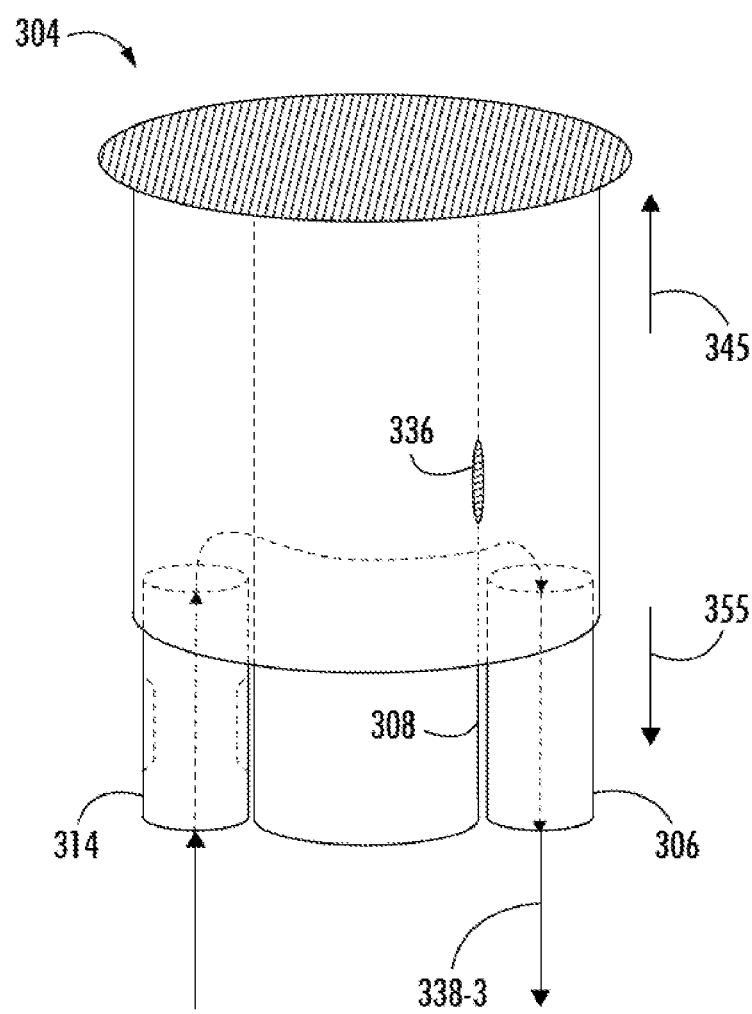

Referring to FIG. 3D, environment 300D illustrates a flow 338-3 through the suction valve well 304 in a balloon channel suction state 305-3. In the balloon channel suction state 305-3, flow 338-3 may enter via the balloon channel 314 and exit through the suction channel 306. Further, in several embodiments, flow may be blocked through the working channel 308 at the well radial hole 336 and may be blocked through the atmospheric channel 316.

Figure 4A:
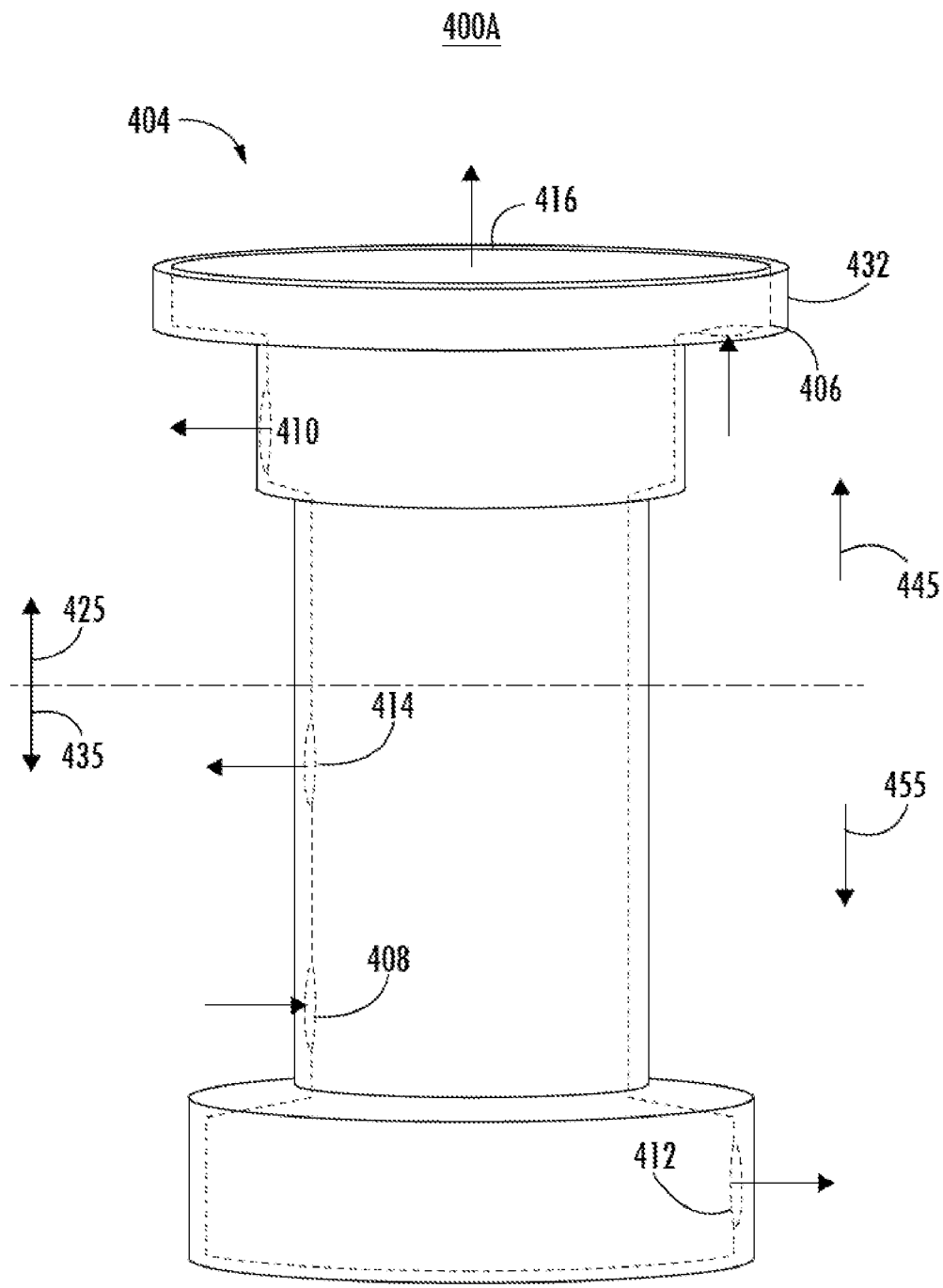
FIGS. 4A-4E illustrate various aspects of an exemplary AW valve well, according to one or more embodiments described herein.

Referring to FIG. 4A, environment 400A illustrates various components of AW valve well 404. The AW valve well 404 may include a top 445 and a bottom 435 and/or an air portion 425 and a water portion 435. The air output channel 410, air input channel 412, and atmospheric channel 416 may be in the air portion 425. The atmospheric channel 416 may comprise a horizontally-oriented exit towards the top 345 and lip 432, the air input channel 412 may comprise a horizontally-oriented entrance towards the top 345, the air output channel 410 may comprise a vertically-oriented exit towards the top. The water input channel 408, water output channel 412, and balloon channel 414 may be in the water portion 435. The balloon channel 414 may comprise a vertically-oriented exit proximate the middle, the water input channel 408 may comprise a vertically-oriented entrance toward the bottom 455, and the water output channel 412 may comprise a vertically-oriented exit toward the bottom 455. In several embodiments, the lip 432 may enable one or more suction valve sets and/or valve interface mechanisms to couple to the AW valve well 404.

In several embodiments, the AW valve well 404 may change diameters one or more times. For example, the diameter changes in conjunction with vertical displacement of a valve may enable flow around the valve and through a channel. In the illustrated embodiment, the AW valve well may have a first diameter comprising the entrance/exits of the air input/atmospheric channels 412, 416, a second diameter comprising the exit of the air output channel 410, a third diameter comprising the entrance/exit of the water input/ balloon channels 408, 414, and a fourth diameter comprising the exit of the water output channel 412. It will be appreciated that the orientation, size, and/or arrangement of one or more of the channels and/or flows may be modified in various embodiments without departing from the scope of this disclosure.

Figure 4B:
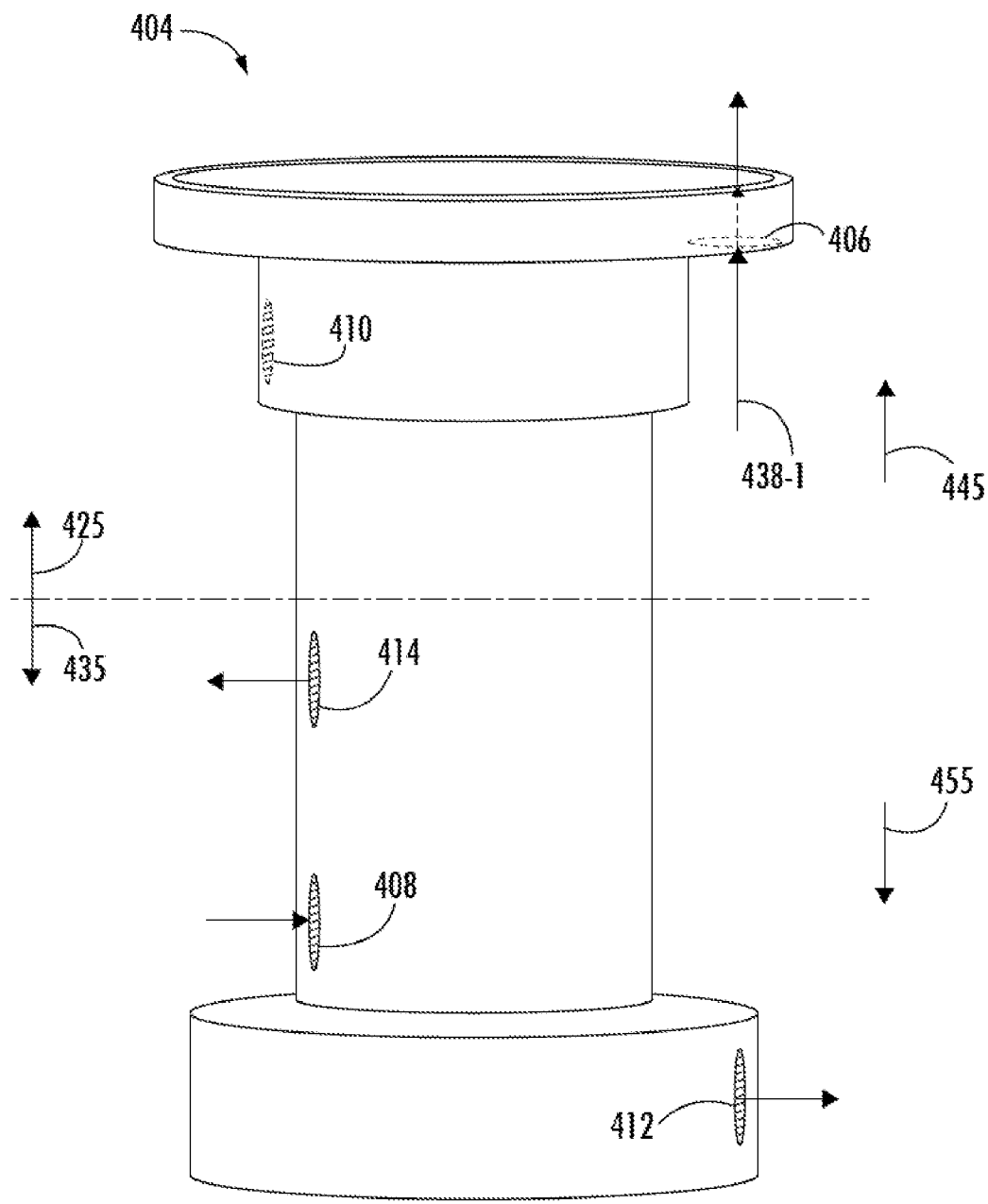

Referring to FIG. 4B, environment 400B illustrates a flow 438-1 through the AW valve well 404 in an air escape state 405-1. In the air escape state 405-1, flow 438-1 may enter via air input channel 406 and exit through the atmospheric channel 416. Further, in some embodiments, flow may be blocked through one or more of balloon channel 414, water input channel 408, and water output channel 412.

Figure 4C:
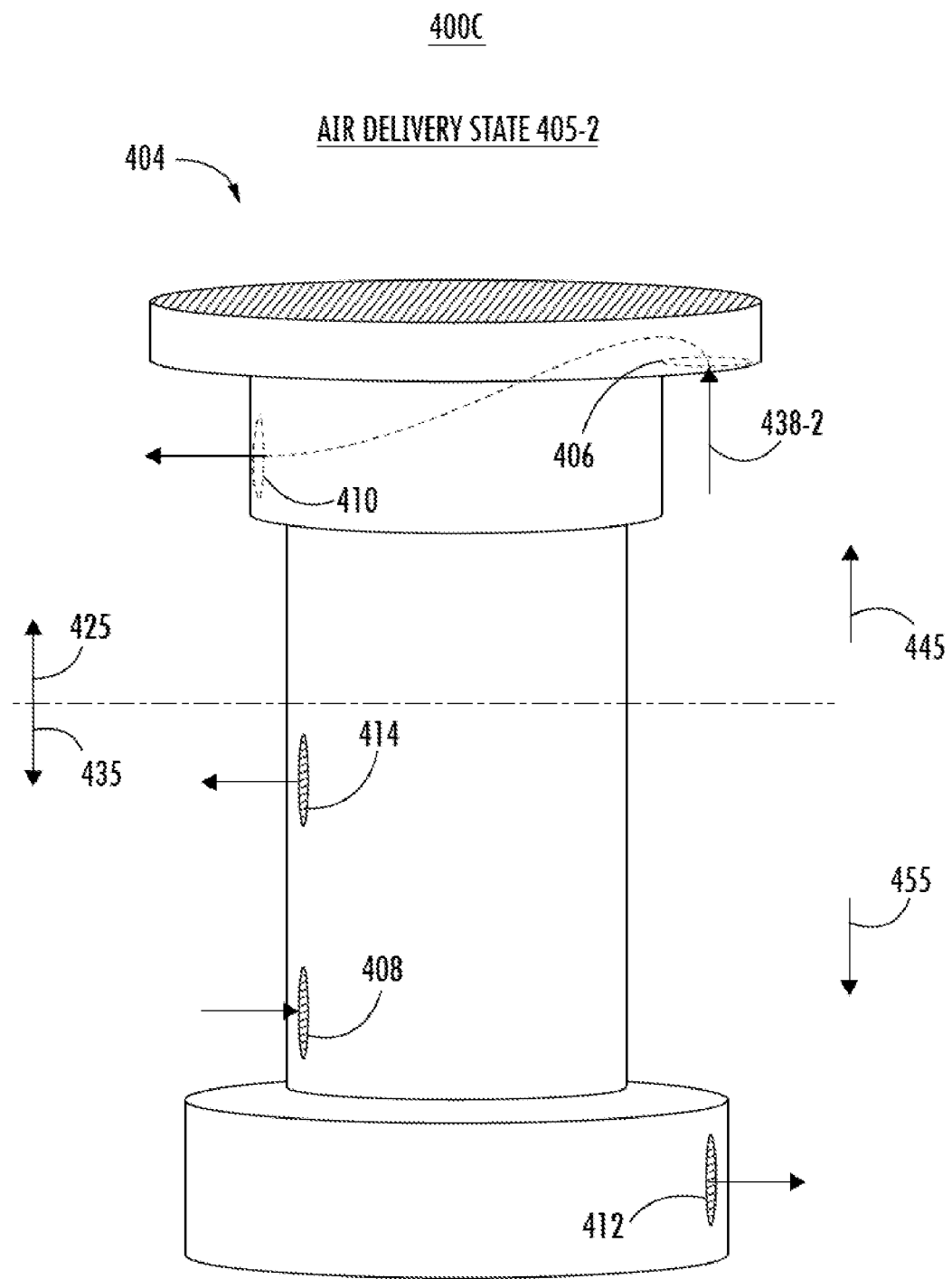

Referring to FIG. 4C, environment 400C illustrates a flow 438-2 through the AW valve well 404 in an air delivery state 405-2. In the air delivery state 405-2, flow 438-2 may enter via the air input channel 406 and exit through the air output channel 410. Further, in various embodiments, flow may be blocked through one or more of atmospheric channel 416, balloon channel 414, water input channel 408, and water output channel 412.

Figure 4D:
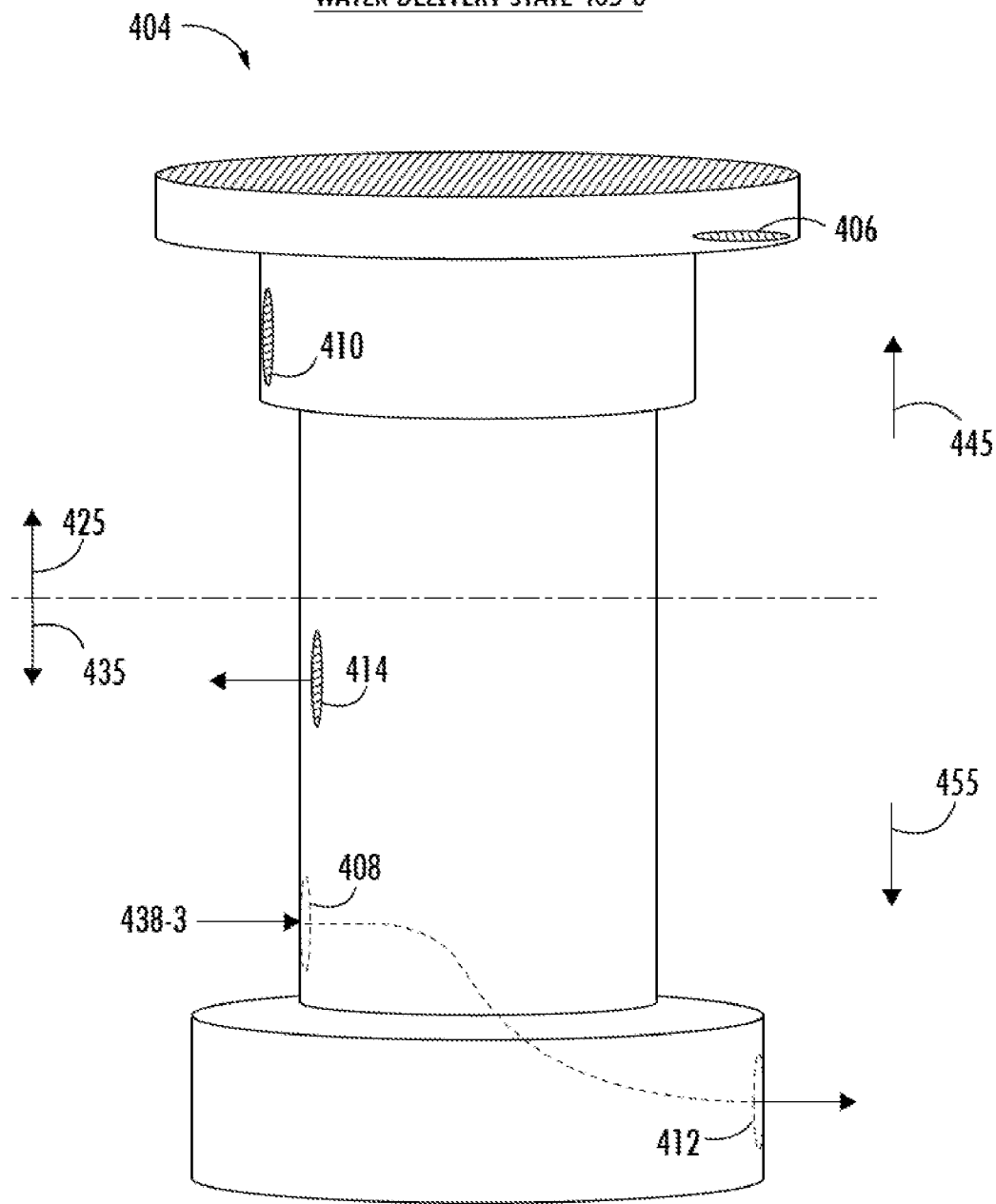

Referring to FIG. 4D, environment 400D illustrates a flow 438-3 through the AW valve well 404 in a water delivery state 405-3. In the water delivery state 405-3, flow 438-3 may enter via water input channel 408 and exit through the water output channel 412. Further, in various embodiments, flow may be blocked through one or more of the balloon channel 414, air output channel 410, air input channel 406, and atmospheric channel 416. In various embodiments, blocking flow at the air input channel 406 may cause pressure to build in a water source feeding the water input channel 408. In various such embodiments, pressure in the water source may cause fluid to flow from the water source to water input channel 408.

Figure 4E:
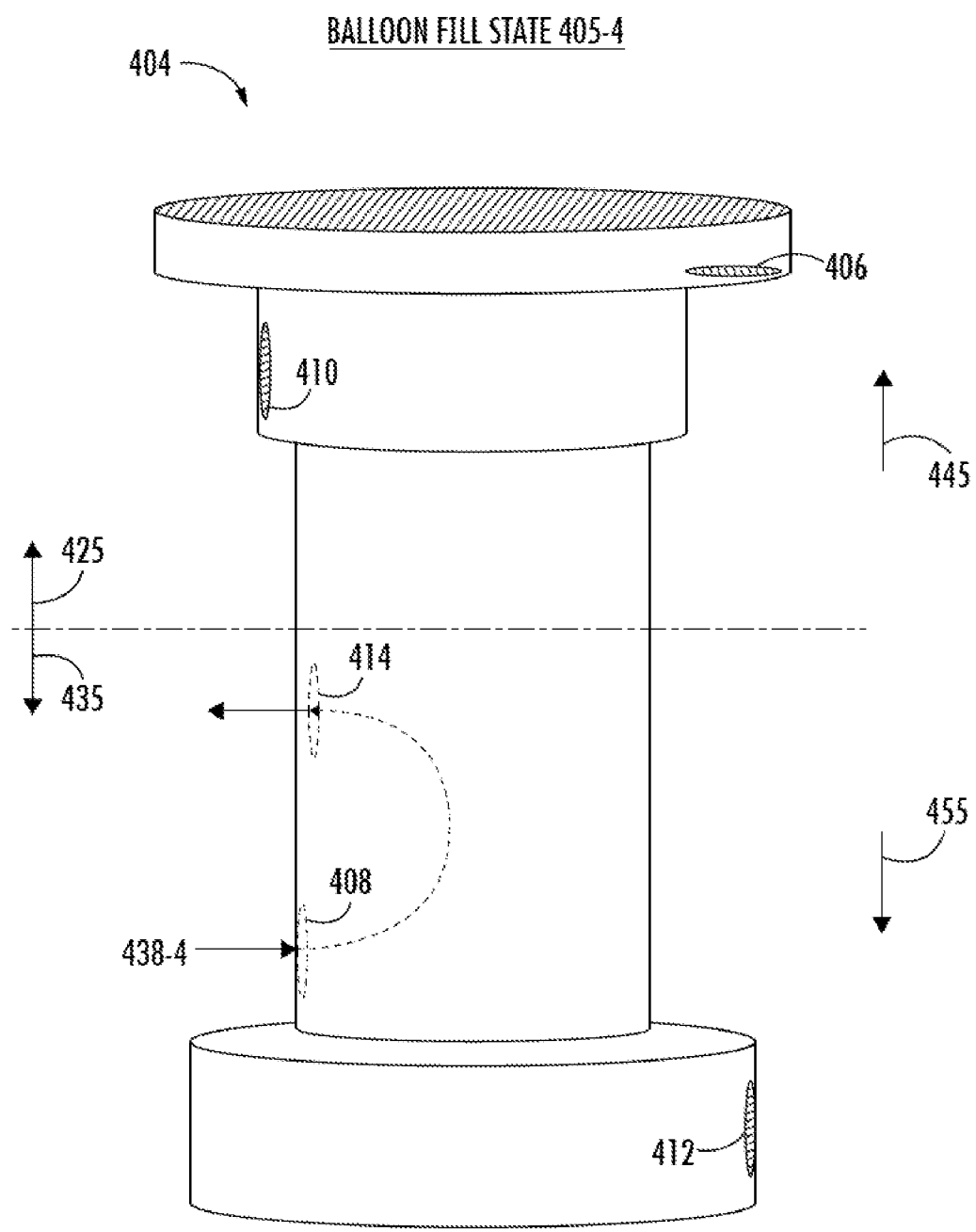

Referring to FIG. 4E, environment 400E illustrates a flow 438-4 through the AW valve well 404 in a balloon fill state 405-4. In the balloon fill state 405-4, flow 438-4 may enter via the water input channel 408 and exit through the balloon channel 414. Further, in many embodiments, flow may be blocked through one or more of the water output channel 412, air output channel 410, air input channel 406, and atmospheric channel 413.

FIGS. 5-12C illustrate various aspects of exemplary valve sets in environments 500, 600A, 600B, 700A, 700B, 800A-C, 900, 1000A, 1000B, 1100A, 1100B, 1200A-C, according to one or more embodiments described herein. In some embodiments, one or more components of FIGS. 5-12C may be the same or similar to one or more other components described herein. Environments 500-800C illustrate various aspects of a suction valve set 518 in conjunction with one or more components of suction valve well 304. Environments 900-1200C illustrate various aspects of an AW valve set 918 in conjunction with one or more components of AW valve well 404. In one or more embodiments described herein, fluid may flow through the valve wells based on the arrangement of one or more valves as positioned by one or more valve interface mechanisms. In many embodiments, one or more valves described herein may include a plurality of components configured to control fluid through a valve well. Embodiments are not limited in this context.

Figure 5:
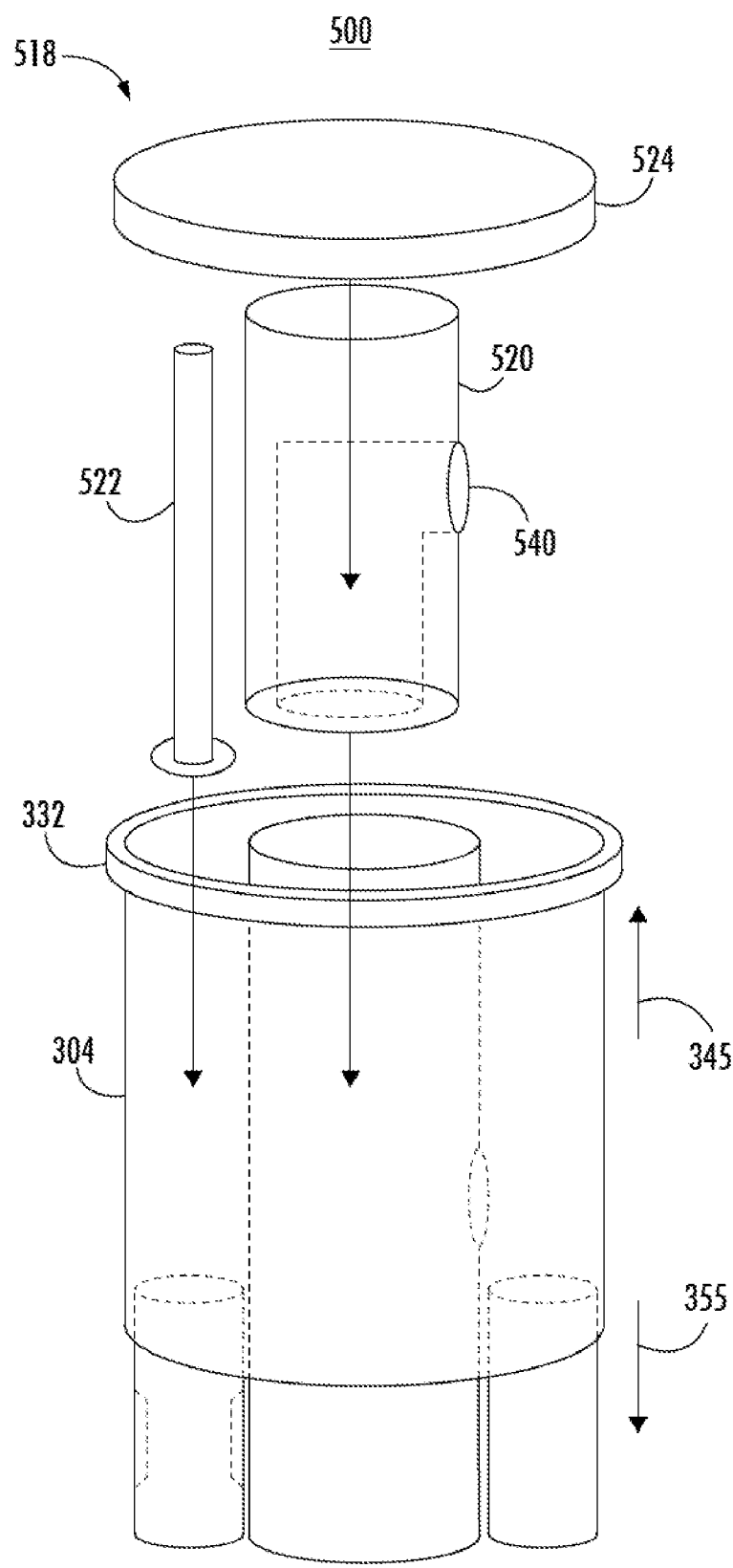
FIG. 5 illustrates an exemplary suction valve set, according to one or more embodiments described herein.

Referring to FIG. 5, environment 500 illustrates suction valve set 518 in conjunction with suction valve well 304. Suction valve set 518 may include working channel valve 520, balloon valve 522, and atmospheric valve 524. The working channel valve 520 may include a working channel valve radial hole 540 that enables fluid to flow into the working channel valve 520 out of the bottom of the working channel valve 520. In several embodiments, the working channel valve 520 may be inserted into the working channel of suction valve well 304 to control flow therethrough. The balloon valve 522 may be inserted into balloon channel 314 of suction valve well 304 to control flow therethrough. The atmospheric valve 524 may be inserted into the atmospheric channel of suction valve well 304 to control flow therethrough. In many embodiments, one or more valves in suction valve set 518 may be integrated with one or more portions of a housing and/or valve interface mechanism corresponding to suction valve well 304.

In one or more embodiments, the atmospheric valve 524 may be configured to control fluid communication with the atmosphere from the interior of the suction valve well 304. In many embodiments, the atmospheric valve 524 may include a hole in a housing. In some embodiments, the atmospheric valve 524 may be operated by covering and/or uncovering the hole, such as with a finger or other mechanism. In several embodiments, the positioning and/or configuration of the valves in suction valve set 518 may be controlled by one or more components of a corresponding valve interface mechanism. For example, depressing a valve interface mechanism to a first stop may simultaneously shut off atmospheric suction via a seal on the underside of a cap and open working channel suction by pushing down the center of the working channel valve 520 to align the working channel valve radial hole 540 and the well radial hole.

Figure 6A:
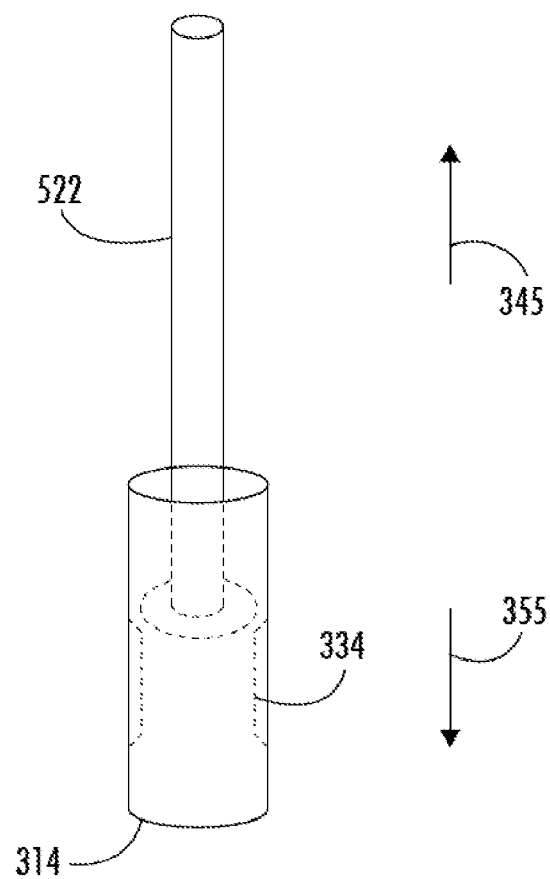
FIGS. 6A-8C illustrate various aspects of exemplary valves in suction valve sets, according to one or more embodiments described herein.
Figure 6B:
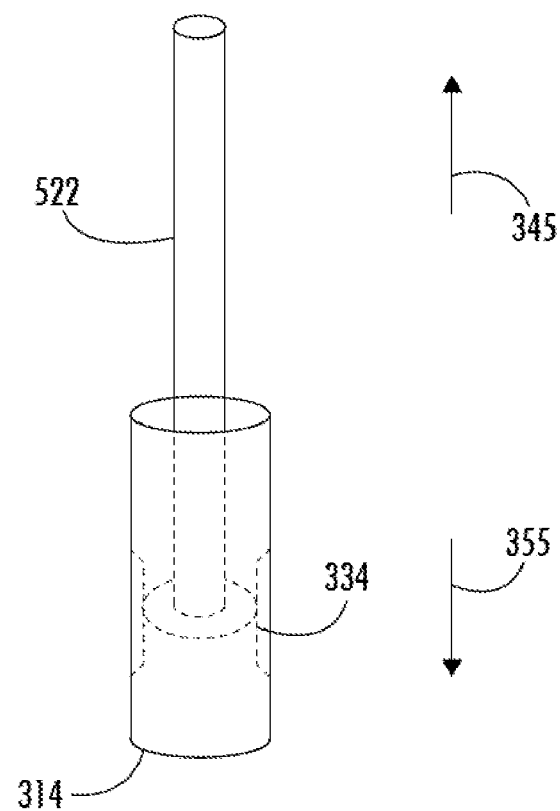

Referring to FIG. 6A, environment 600A illustrates a balloon valve open state 615-1. In the balloon valve open state 615-1, the balloon valve 522 may allow flow through the balloon channel 314 by permitting flow through the necking portion 334 of balloon channel 314. Referring to FIG. 6B, environment 600B illustrates a balloon valve sealed state 615-2. In the balloon valve sealed state 615-2, the balloon valve 522 may prevent flow through balloon channel 314 by blocking flow through the necking portion 334 of balloon channel 314. In additional, or alternative embodiments, the default state of the balloon valve 522 may be the balloon valve sealed state 615-2 and the balloon valve 522 may be depressed toward the bottom 355 and below the necking portion 334 to transition into the balloon valve open state 615-1.

Figure 7A:
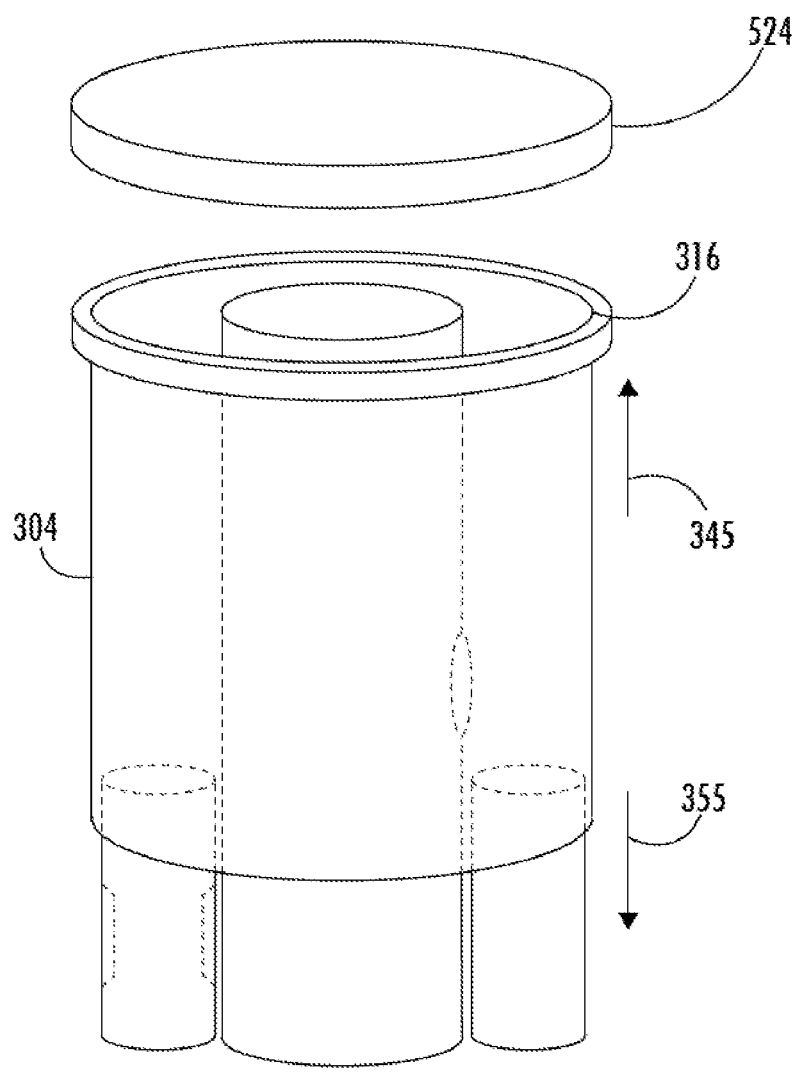
Figure 7B:
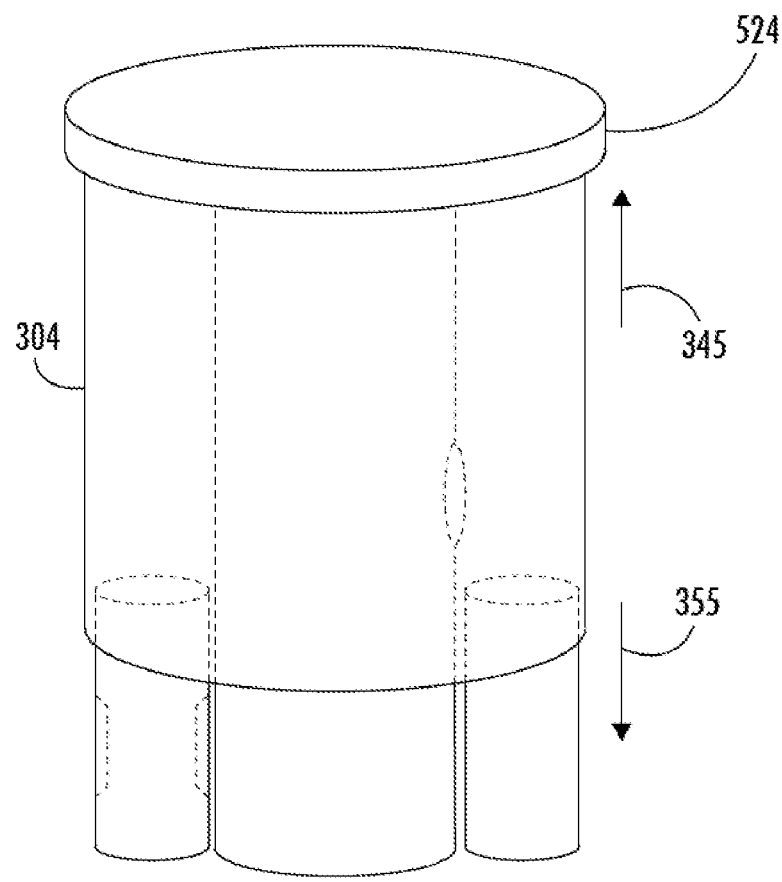

Referring to FIG. 7A, environment 700A illustrates an atmospheric valve open state 715-1. In the atmospheric valve open state 715-1, the atmospheric valve 524 may allow flow through the atmospheric channel 316 of suction valve well 304. Referring to FIG. 7B, environment 700B illustrates an atmospheric valve sealed state 715-2. In the atmospheric valve sealed state 715-2, the atmospheric valve 524 may prevent flow through atmospheric channel 316. As will be discussed in more detail below, in operation, fluid communication with the atmosphere may be provided through a passage/channel in, or created by, one or more components. Further, one or more components may be used to seal portions of the atmospheric channel 316 to facilitate control of fluid communication with the atmosphere by atmospheric valve 524. In some embodiments, atmospheric valve 524 may include a plurality of components configured to control fluid communication with the atmosphere.

Figure 8A:
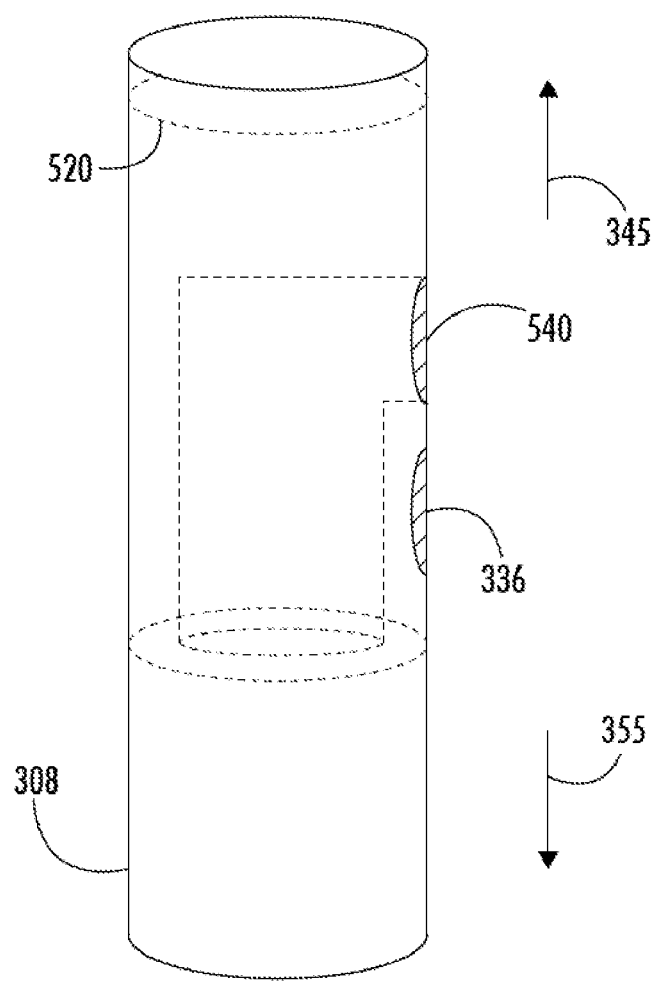
Figure 8B:
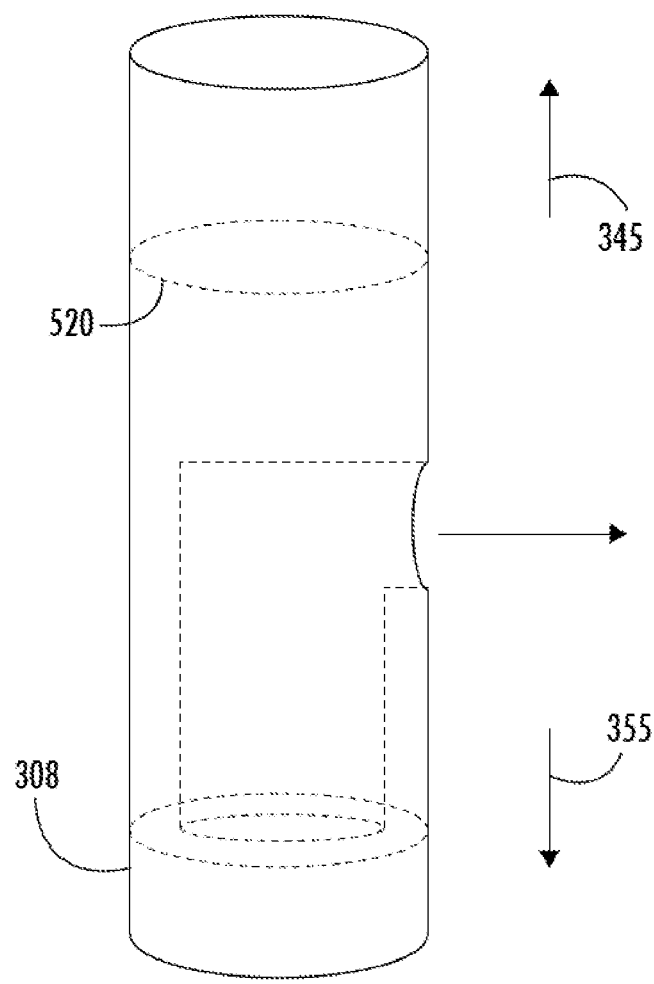
Figure 8C:
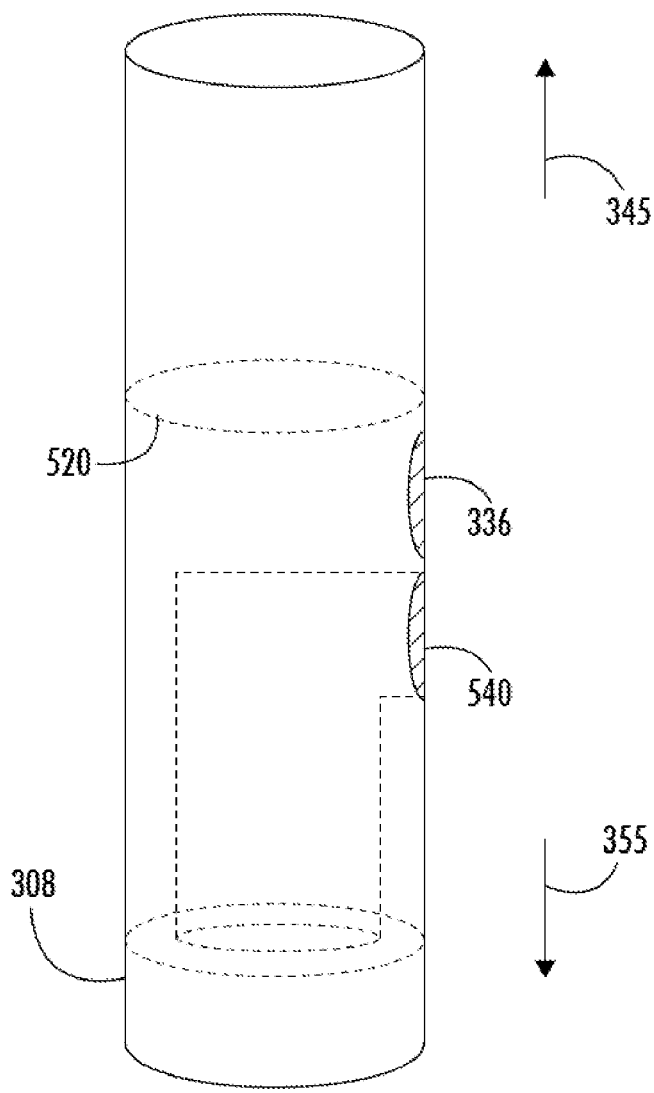

Referring to FIG. 8A, environment 800A illustrates a working channel valve first sealed state 815-1. In the working channel valve first sealed state 815-1, the working channel valve 520 may prevent flow through well radial hole 336 by misaligning the working channel valve radial hole 540 with the well radial hole 336, such as with working channel valve 520 being positioned such that working channel valve radial hole 540 is above well radial hole 336. Referring to FIG. 8B, environment 800B illustrates a working channel valve open state 815-2. In the working channel valve open state 815-2, the working channel valve radial hole 540 and the well radial hole 336 may be aligned to permit suction flow through working channel 308. For example, the flow may enter through the bottom of the working channel valve 520 and exit through the well radial hole 336. Referring to FIG. 8C, environment 800C illustrates a working channel valve second sealed state 815-3. In the working channel valve second sealed state 815-3, the working channel valve 520 may prevent flow through well radial hole 336 by misaligning the working channel valve radial hole 540 with the well radial hole 336, such as with working channel valve 520 being positioned such that working channel radial hole 440 is below well radial hole 336.

Figure 9:
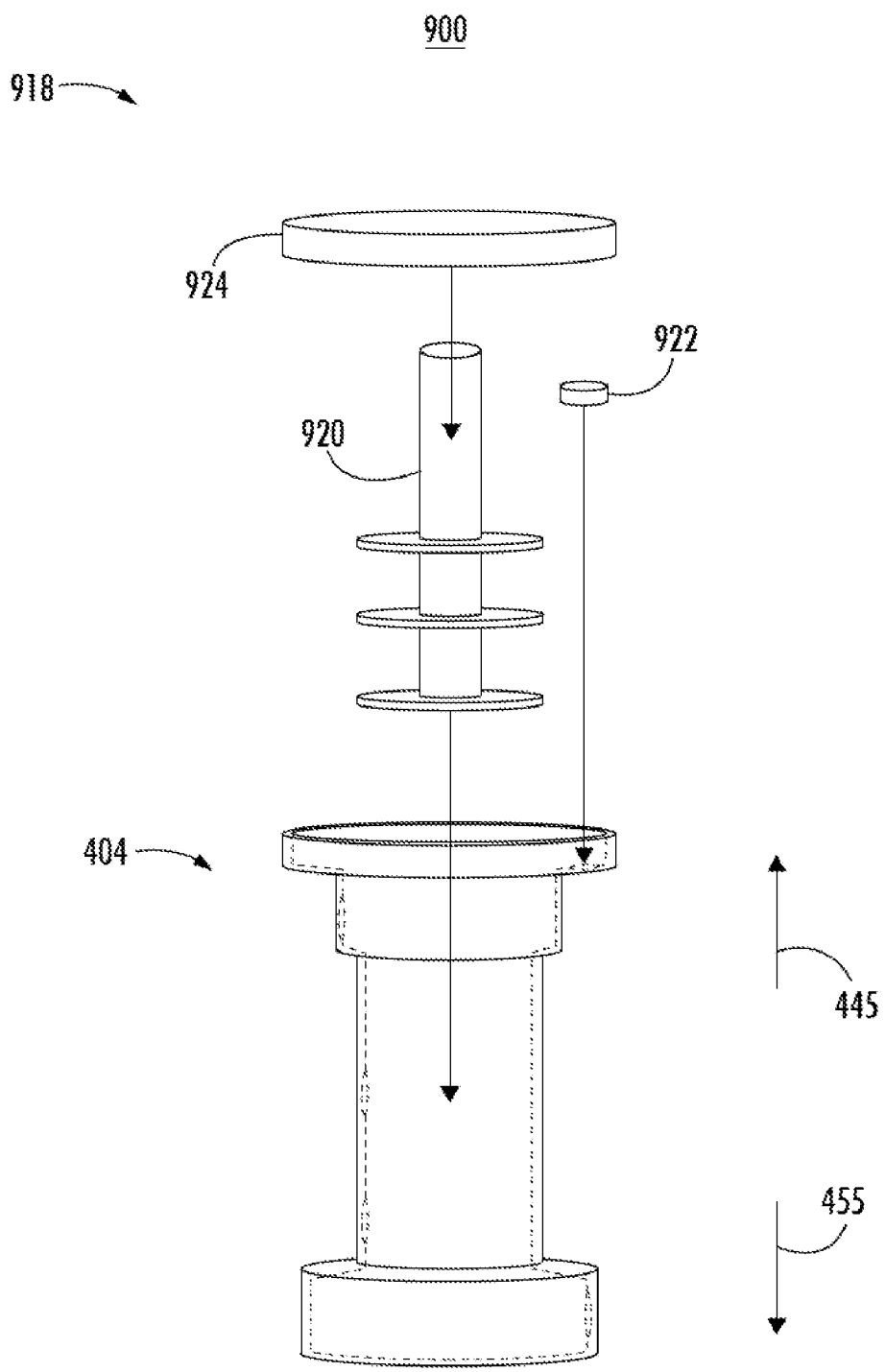
FIG. 9 illustrates an exemplary AW valve set, according to one or more embodiments described herein.

Referring to FIG. 9, environment 900 illustrates AW valve set 918 in conjunction with AW valve well 404. AW valve set 918 may include primary control valve 920, air input valve 922, and atmospheric valve 924. In several embodiments, the primary control valve 920 may be inserted into the AW valve well 404 to control, at least in part, the flow through one or more channels of the AW valve well 404. In various embodiments, the air input valve 922 may be inserted into the air input channel of the AW valve well 404 to control flow therethrough. In many embodiments, the atmospheric valve 924 may be inserted into the atmospheric channel of AW valve well 404 to control flow therethrough. In many embodiments, one or more valves in AW valve set 918 may be integrated with one or more portions of a housing and/or valve interface mechanism corresponding to AW valve well 404.

In one or more embodiments, the atmospheric valve 924 may be configured to control fluid communication with the atmosphere from the interior of the AW valve well 404. In many embodiments, the atmospheric valve 924 may include a hole in a housing. In some embodiments, the atmospheric valve 924 may be operated by covering and/or uncovering the hole, such as with a finger or other mechanism. In several embodiments, the positioning and/or configuration of the valves in AW valve set 918 may be controlled by one or more components of a corresponding valve interface mechanism. In some embodiments, one or more portions of the atmospheric channel 416 may be included in the primary control valve 920. In some such embodiments, the atmospheric channel 416 may comprise one or more passages through at least a portion of the primary control valve 920. For example, the atmospheric channel 416 may comprise a hole in the top of the primary control valve 920 in fluid communication with a radial hole in the primary control valve 920 proximate the air input channel 406. In such examples, covering the hole may direct air flow into the air output channel 410 and down a working channel of an endoscope.

Figure 10A:
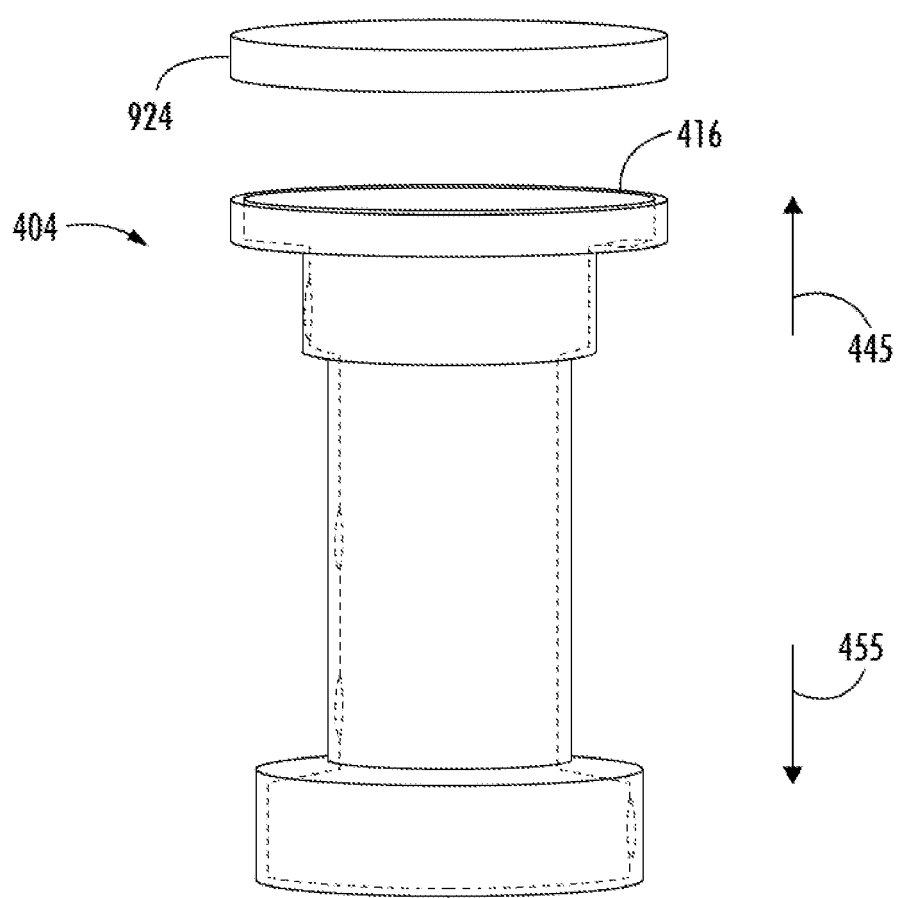
FIGS. 10A-12C illustrate various aspects of exemplary valves in AW valve sets, according to one or more embodiments described herein.
Figure 10B:
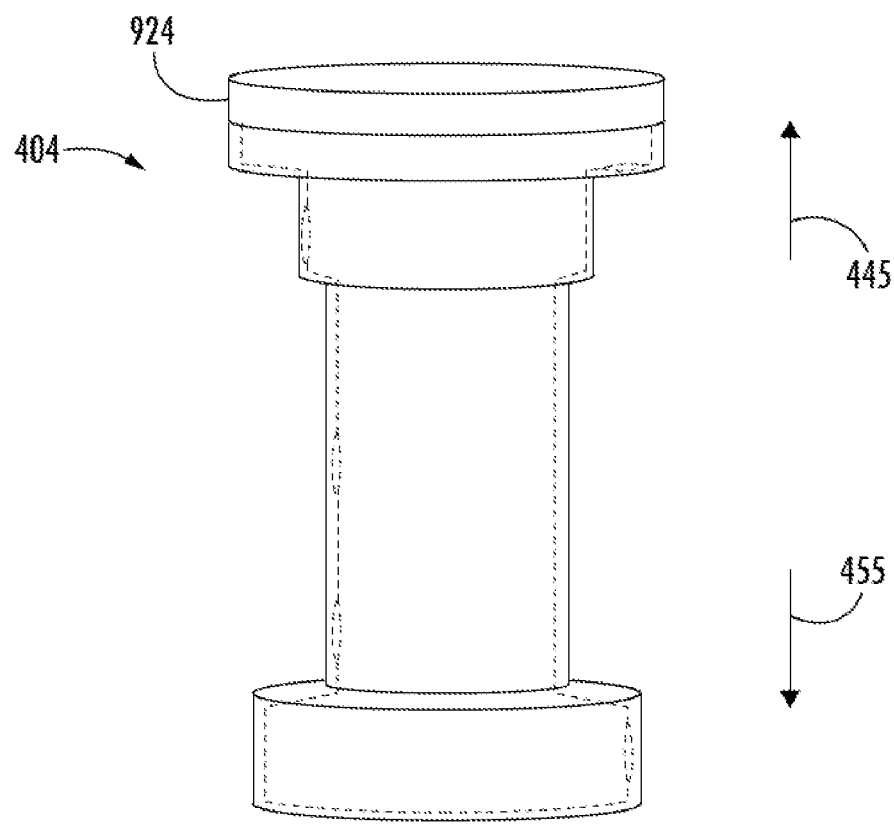

Referring to FIG. 10A, environment 1000A illustrates an atmospheric valve open state. In the atmospheric valve open state, the atmospheric valve 924 may allow flow through the atmospheric channel of AW valve well 404. Referring to FIG. 10B, environment 1000B illustrates an atmospheric valve sealed state 1015-2. In the atmospheric valve sealed state 1015-2, the atmospheric valve 924 may prevent flow through atmospheric channel of AW valve well 404. As will be discussed in more detail below, in operation, fluid communication with the atmosphere may be provided through a passage/channel in, or created by, one or more components (e.g., primary control valve 920). Further, one or more components may be used to seal portions of the atmospheric channel 316 to facilitate control of fluid communication with the atmosphere by atmospheric valve 924. In some embodiments, atmospheric valve 924 may include a plurality of components configured to control fluid communication with the atmosphere.

Figure 11A:
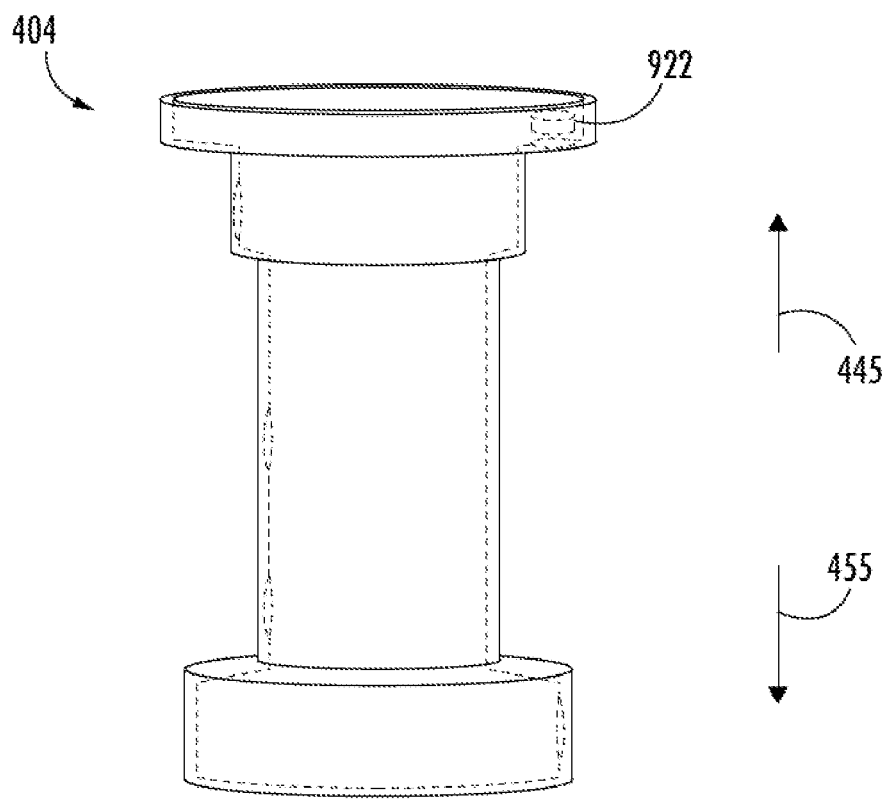
Figure 11B:
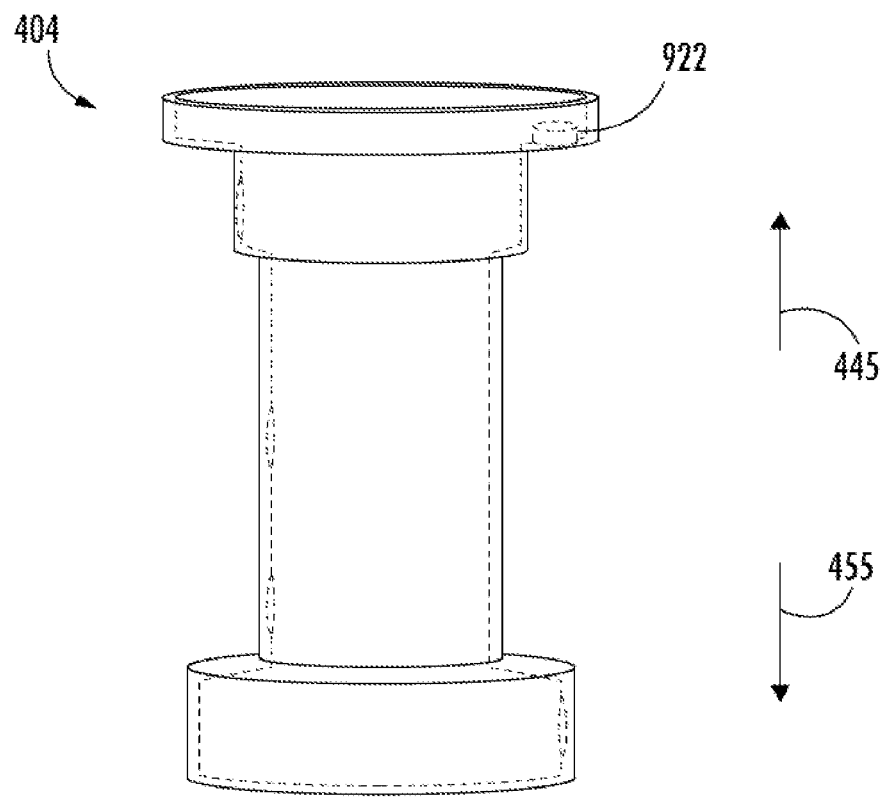

Referring to FIG. 11A, environment 1100A illustrates an air input valve open state 1115-1. In the air input valve open state 1115-1, the air input valve 522 may allow flow through the air input channel of AW valve well 404. Referring to FIG. 11B, environment 1100B illustrates an air input valve sealed state 1115-2. In the air input valve sealed state 1115-2, the air input valve 922 may prevent flow through the air input channel of AW valve well 404. In some embodiments, sealing the air input channel may cause a fluid source (e.g., water reservoir) to be pressurized, thereby enabling/causing fluid to flow into the AW valve well 404 via water input channel 408.

Figure 12A:
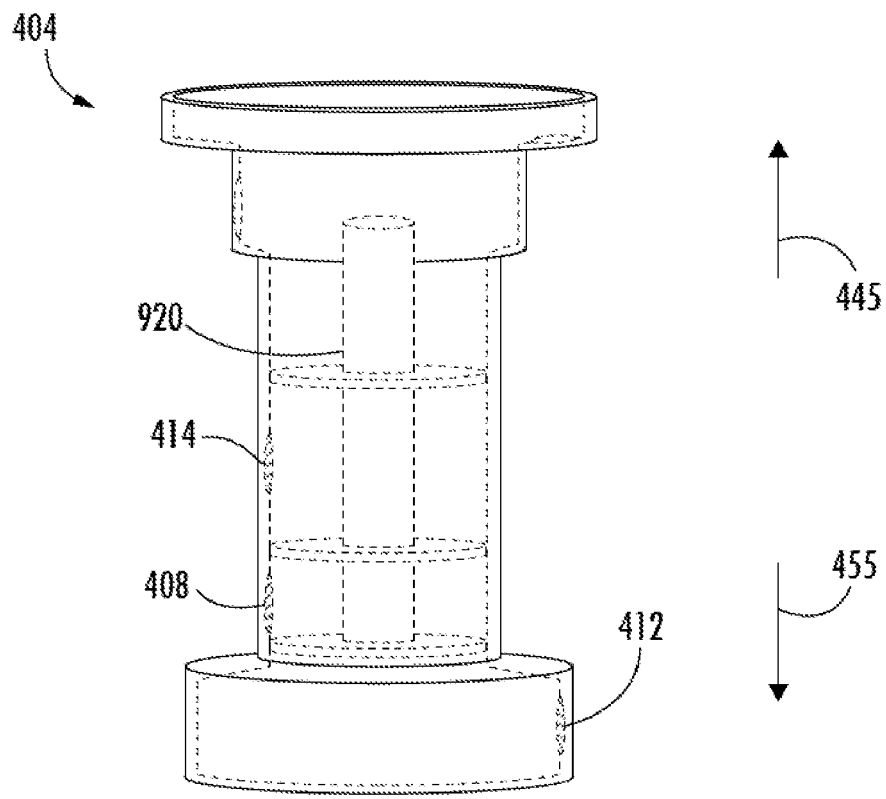
Figure 12B:
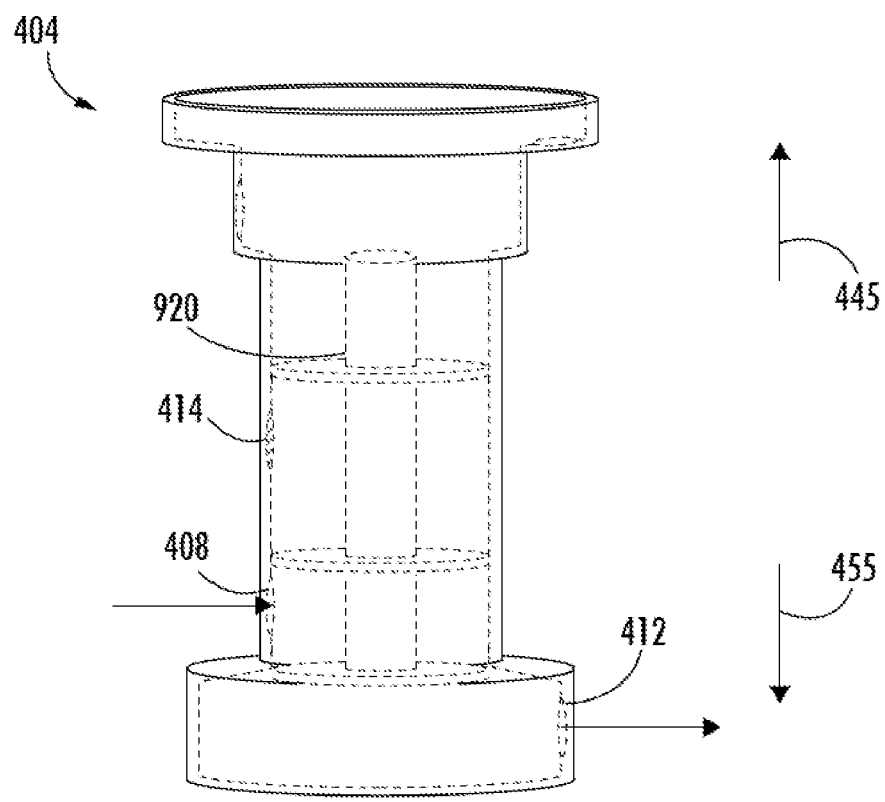
Figure 12C:
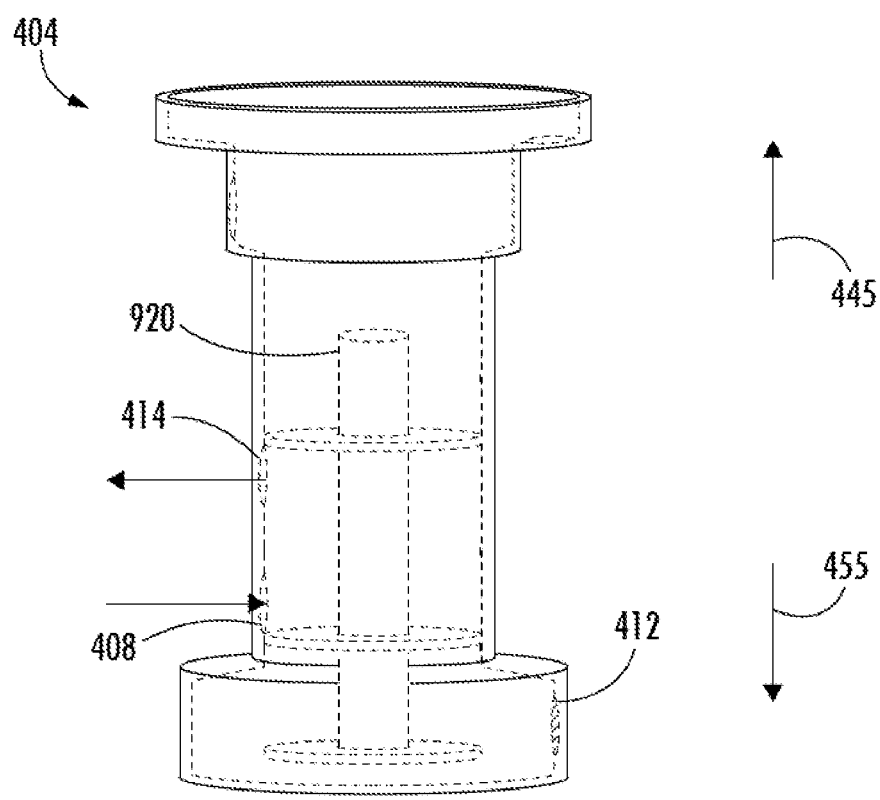

Referring to FIG. 12A, environment 1200A illustrates a primary valve sealed state 1215-1. In the primary valve sealed state 1215-1, the primary control valve 920 may prevent flow through one or more of the balloon channel 414, water input channel 408, and water output channel 412. Referring to FIG. 12B, environment 1200B illustrates a primary valve water output state 1215-2. In the primary valve water output state 1215-2, the primary control valve 920 may be positioned to block flow through balloon channel 414 and permit flow from water input channel 408 to water output channel 412. In various embodiments, primary control valve 920 may utilize changes in diameter in AW valve well 404 to control flow. Referring to FIG. 12C, environment 1200C illustrates a primary valve balloon fill state 1215-3. In the primary valve balloon fill state 1215-3, the primary control valve 920 may be positioned to block flow through water output channel 412 and permit flow from water input channel 408 to balloon channel 414. In various embodiments, one or more features of primary control valve 920 may operate as valves for multiple channels. In some embodiments, one or more features of primary control valve 920 may comprise one or more channels, or one or more portions thereof. For example, primary control valve 920 may comprise atmospheric channel 416.

Figure 13:
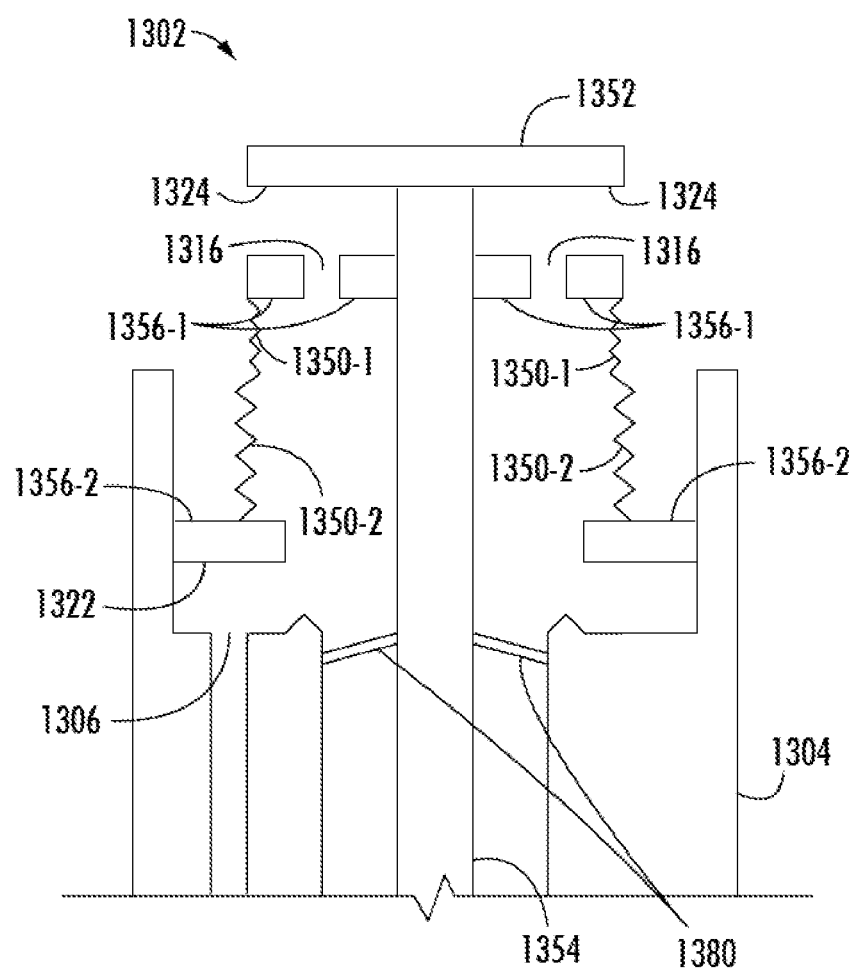
FIG. 13 illustrates various aspects of an exemplary AW valve assembly, according to one or more embodiments described herein.

FIG. 13 illustrates various aspects of an exemplary AW valve assembly 1302 in environment 1300, according to one or more embodiments described herein. In many embodiments, a cross section of one or more portions of AW valve assembly 1302 may be illustrated in environment 1300. In some embodiments, one or more components of FIG. 13 may be the same or similar to one or more other components described herein. AW valve assembly 1302 includes an AW valve well 1304, an AW valve set, and a valve interface mechanism. The illustrated portion of the AW valve well 1304 includes air input channel 1306. In various embodiments, flapper valve 1380 may couple to AW valve well 1304. The illustrated portion of the AW valve set may include air input valve 1322 and atmospheric valve 1324. In several embodiments, linkage 1354 may be coupled to and/or include one or more portions of a primary control valve in the AW valve set. In many embodiments, one or more portions of one or more valves in the valve set may include, or be included in, one or more portions of the valve interface mechanism. The illustrated portion of the valve interface mechanism includes interface 1352 with atmospheric valve 1324, linkage 1354, linkage 1356-1 with atmospheric channel 1316, and linkage 1356-2 with air input valve 1322. In one or more embodiments described herein, interface 1352 may be moved to control the flow of fluid through AW valve assembly 1302, such as by switching between an air escape state, an air delivery state, a water delivery state, and a balloon fill state. Embodiments are not limited in this context.

In various embodiments, linkage 1356-1 comprising atmospheric channel 1316 may be coupled to linkage 1356-2 comprising air input valve 1322 via bellows 1350. In various embodiments, the bellows 1350 may be constructed from a flexible and/or elastic material. In many embodiments, bellow 1350-1 and bellow 1350-2 may provide different amounts of biasing force. In many such embodiments, the differing amounts of biasing force may be utilized to provide tactile feedback comprising indications of the state of AW valve assembly 1302. In some embodiments, the bellows 1350 may comprise, or be biased upward, by two springs disposed in series. In such embodiments, the two springs may have different spring constants.

In one or more embodiments, bellows 1350-1 may function based on air pressure due to flow from air input channel 1306. In several embodiments, flapper valve 1380 may include a one-way valve. In several such embodiments, the one-way valve may be configured to open when air pressure is applied. For example, a buildup of pressure from air input channel 1306 when atmospheric channel 1316 is sealed by atmospheric valve 1324 may cause the flapper valve 1380 to open. In such examples, when the flapper valve 1380 is open air may flow distally past flapper valve 1380 and exit the AW valve well via an air output channel (see e.g., FIG. 4C). In other embodiments, the one-way valve may be configured to open when air pressure is removed. In some embodiments, atmospheric channel 1316 may be sized to sufficiently restrict flow from air input channel 1306 to achieve an operational pressure for the bellows 1350.

In many embodiments, interface 1352 may be coupled to linkage 1354. In many such embodiments, linkage 1354 may comprise a proximal portion of a primary control valve (see e.g., FIGS. 12A-12C). In various embodiments, interface 1352, or interface member, may include a knob, button, and/or cap. In various embodiments, the linkage 1354 may be attached to, or included in, a primary control valve in AW valve assembly 1302. In several embodiments, flapper valve 1380 may create a seal between linkage 1354 and AW valve well 1304. In some embodiments, flapper valve 1380 may be coupled to linkage 1354.

In several embodiments, when AW valve assembly 1302 is in the air escape state, fluid may flow in the air input channel 1306 and out the atmospheric channel 1316. In several such embodiments, a biasing member, such as a spring (not shown), may bias the bellows 1350 and/or the linkage 1356-1 upward (e.g., in a vector normal to the bottom surface of the AW valve well 1304). In many such embodiments, the flow exiting atmospheric channel 1316 may float or bias the interface 1352 upward. For instance, a biasing member may include a pressure differential between the atmosphere and the atmospheric channel. In such instances, this pressure differential may force the atmospheric valve 1324 upward in the absence of a downward force against interface 1352, such as user input. In other words, exposing a top portion of the atmospheric valve 1324 (e.g., interface 1352) to atmospheric pressure and a bottom portion of the atmospheric valve to an atmospheric channel pressure greater than the atmospheric pressure may bias the atmospheric valve upward. In other embodiments, a spring or other type of biasing member may bias the interface 1352 upward. Accordingly, when a user pushes down, they may overcome the air pressure and/or the spring force biasing the interface 1352 and/or atmospheric valve 1324 to seal the atmospheric channel 1316.

In many embodiments, when AW valve assembly 1302 is in the air delivery state, interface 1352 may be depressed to cause atmospheric valve 1324 to seal atmospheric channel 1316 and cause fluid to flow in the air input channel 1306 and out the air output channel (not shown). In many such embodiments, the flow may cause bellows 1350 to bias the interface 1352 upward (e.g., in a vector normal to the bottom surface of the AW valve well 1304).

In some embodiments, when AW valve assembly 1302 is in the water delivery state, interface 1352 may be depressed such that bellow 1350-1 compresses, air input valve 1322 moves down to seal air input channel 1306, and linkage 1354 positions the primary control valve to place the water input channel and the water output channel of AW valve well 1304 in fluid communication. In some such embodiments, sufficient pressure for operation of bellows 1350 may be maintained via the sealed air input channel 1306, the sealed atmospheric channel 1316, and flapper valve 1380. In many embodiments, bellow 1350-1 may compress prior to appreciable compression of bellow 1350-2 due to the difference in biasing forces. The differing biasing forces may provide feedback, such as tactile and/or haptic information. In many embodiments, the feedback may include a change in resistance at a transition between different flow states.

In some embodiments, when AW valve assembly 1302 is in the balloon fill state, interface 1352 may be depressed such that bellow 1350-1 compresses, bellow 1350-2 compresses, air input valve 1322 seals air input channel 1306, and linkage 1354 positions the primary control valve to place the water input channel and the balloon channel of AW valve well 1304 in fluid communication. In some such embodiments, sufficient pressure for operation of bellows 1350 may be maintained via the sealed air input channel 1306, the sealed atmospheric channel 1316, and flapper valve 1380. In many embodiments, bellow 1350-1 may compress prior to appreciable compression of bellow 1350-2 due to the difference in biasing forces.

Figure 14:
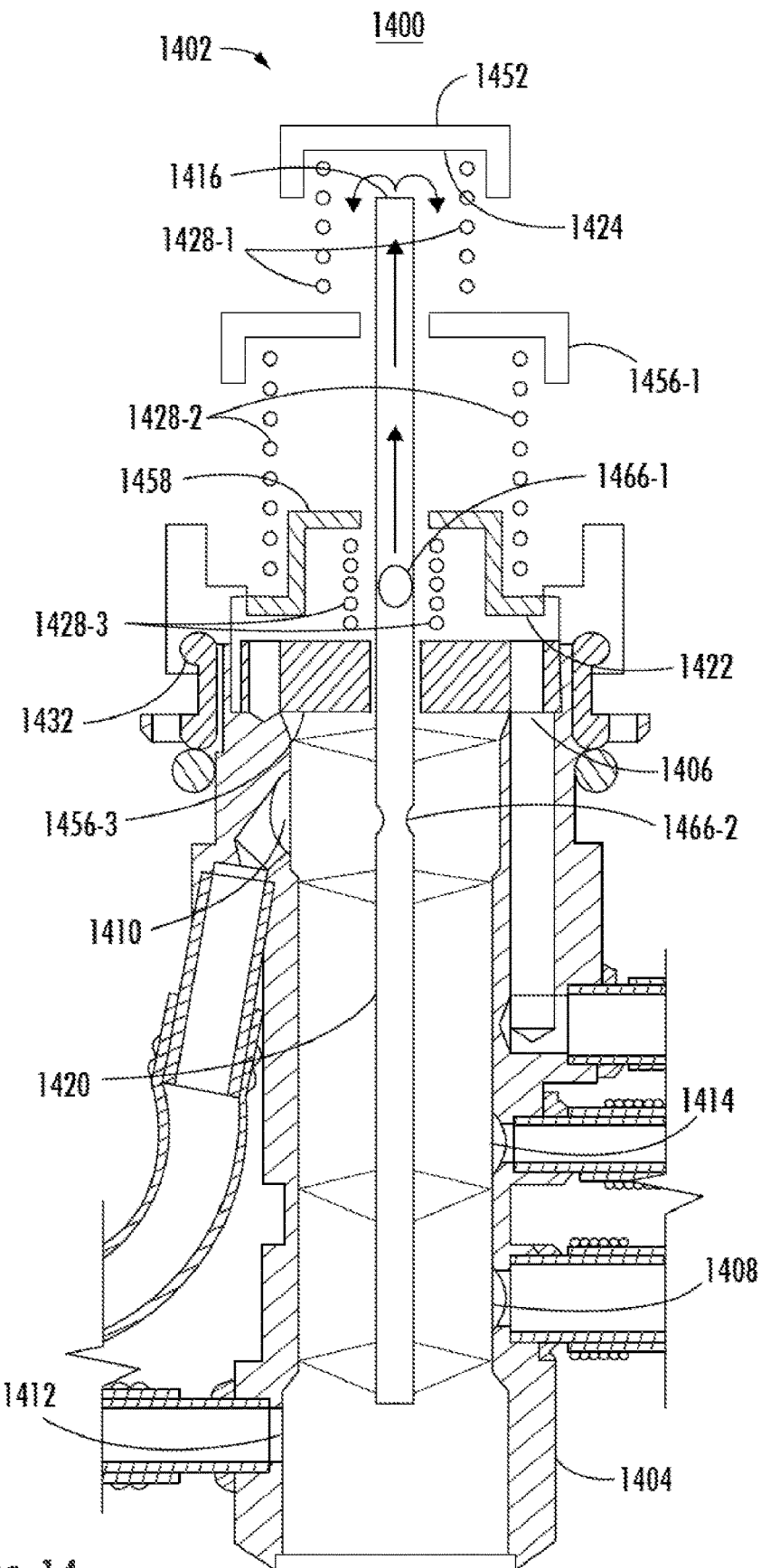
FIG. 14 illustrates various aspects of an exemplary AW valve assembly, according to one or more embodiments described herein.

FIG. 14 illustrates various aspects of an exemplary AW valve assembly 1402 in environment 1400, according to one or more embodiments described herein. In many embodiments, a cross section of one or more portions of AW valve assembly 1402 may be illustrated in environment 1400. In some embodiments, one or more components of FIG. 14 may be the same or similar to one or more other components described herein. AW valve assembly 1402 includes an AW valve well 1404, an AW valve set, and a valve interface mechanism. The AW valve well 1404 includes air input channel 1406, water input channel 1408, air output channel 1410, water output channel 1412, balloon channel 1414, and lip 1432. The AW valve set may include primary control valve 1420 with radial air holes 1466-1, 1466-2 and atmospheric channel 1316, air input valve 1422, and atmospheric valve 1424. In the illustrated embodiment, the air input valve 1422 and the atmospheric valve 1424 may include, or be included in, one or more portions of the valve interface mechanism. The valve interface mechanism includes biasing members 1428-1, 1428-2, 1428-3, interface 1452 with atmospheric valve 1424, linkages 1456-1, 1456-2, 1456-3, and hat 1458. In one or more embodiments described herein, interface 1452 may be moved to control the flow of fluid through AW valve assembly 1402, such as by switching between an air escape state, an air delivery state, a water delivery state, and a balloon fill state. Embodiments are not limited in this context.

In various embodiments, linkage 1456-1 may be coupled to primary control valve 1420. In various such embodiments, linkage 1456-1 may be coupled to interface 1452 via biasing member 1428-1, further, linkage 1456-1 may be coupled to hat 1458 via biasing member 1428-2. In some embodiments, interface 1352 may include a knob, button, and/or cap. In several embodiments, hat 1458 may be coupled to the AW valve well 1404 via linkage 1456-2. In many embodiments, hat 1458 may be coupled to linkage 1456-3 via biasing member 1428-3. In one or more embodiments, linkage 1456-3 may seat in the AW valve well 1404 to enable biasing member 1428-3 to push against hat 1458, which in turn can enable biasing member 1428-2 to push against linkage 1456-1, which in turn can enable biasing member 1428-1 to push against interface 1452. In many embodiments, the set of biasing members 1428 may operate to bias the AW valve assembly into the air escape state.

In one or more embodiments described herein, coupling may refer to a connection between two components. In one or more such embodiments, the coupling may be via a third component. For example, reference to a biasing member coupling first and second components may indicate that the biasing member seats between the first and second components. In such examples, the biasing member may be compressed between the first and second components, such as in response to user input.

In several embodiments, when AW valve assembly 1402 is in the air escape state, fluid may flow in the air input channel 1406 and out the atmospheric channel 1416. In several such embodiments, the flow may flow from air input channel 1406, through linkage 1456-3, into radial hole 1466-1, and out of the atmospheric channel 1416. In some embodiments, linkage 1456-3 may include a disc with a plurality of holes configured to distribute flow from air input channel 1406.

In many embodiments, when AW valve assembly 1402 is in the air delivery state, interface 1452 may be depressed to cause atmospheric valve 1344 to seal atmospheric channel 1416 and cause fluid to flow in the air input channel 1406 and out the air output channel 1410. In many such embodiments, biasing member 1428-1 may compress to enable atmospheric valve 1424 to seal with atmospheric channel 1416.

In some embodiments, when AW valve assembly 1402 is in the water delivery state, interface 1452 may be depressed to compress biasing member 1428-1 and cause atmospheric valve 1344 to seal atmospheric channel 1416, compress biasing member 1428-3 and cause air input valve 1422 to seal air input channel 1406, and position primary control valve 1420 to place water input channel 1408 in fluid communication with water output channel 1412. In such embodiments, fluid may flow in the water input channel 1408 and out the water output channel 1412.

In various embodiments, when AW valve assembly 1402 is in the balloon fill state, interface 1452 may be depressed to compress biasing member 1428-1 and cause atmospheric valve 1344 to seal atmospheric channel 1416, compress biasing member 1428-3 and cause air input valve 1422 to seal air input channel 1406, compress biasing member 1428-2 to position primary control valve 1420 to place water input channel 1408 in fluid communication with balloon channel 1414. In such embodiments, fluid may flow in the water input channel 1408 and out the balloon channel 1414.

In many embodiments, the biasing force and/or resistance to compression of each of the biasing members may be determined for intuitive and reliable operation with smooth and efficient state transitions. For instance, biasing members 1428 may include first, second, and third springs (1428-1, 1428-2, 1428-3, respectively). The first spring may have the lowest spring rate, the second spring may have the highest spring rate, and the third spring having a middle spring rate.

Figure 15:
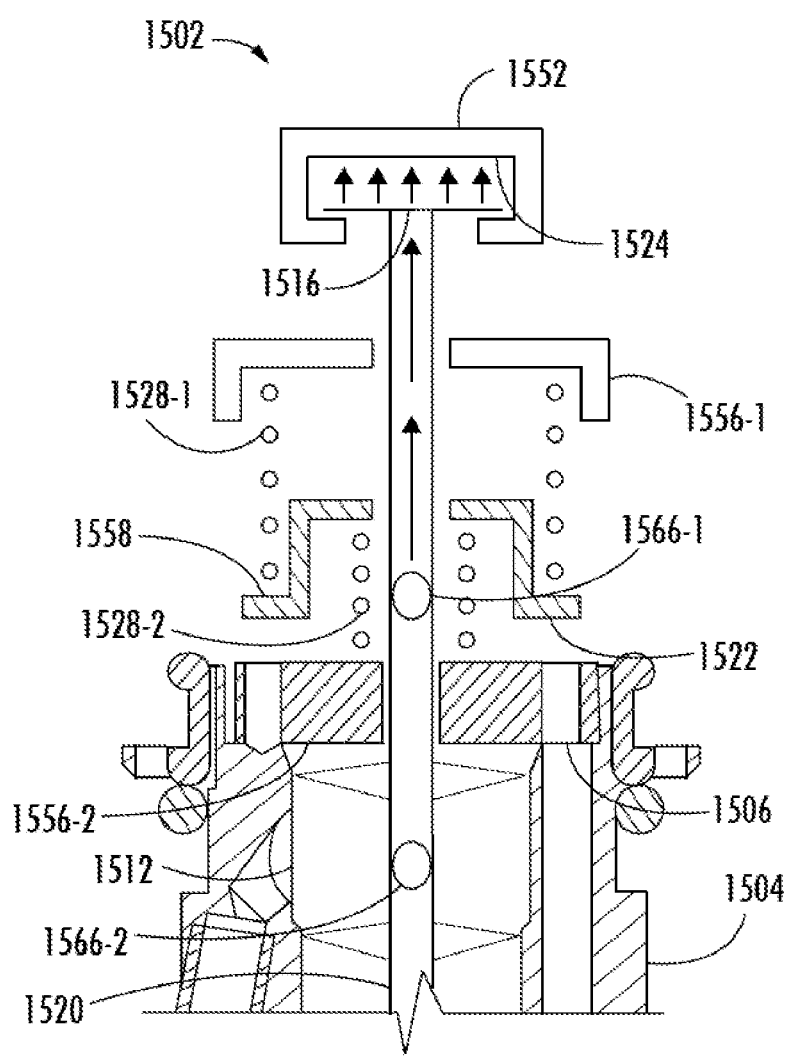
FIG. 15 illustrates various aspects of an exemplary AW valve assembly, according to one or more embodiments described herein.

FIG. 15 illustrates various aspects of an exemplary AW valve assembly 1502 in environment 1500, according to one or more embodiments described herein. In many embodiments, a cross section of one or more portions of AW valve assembly 1502 may be illustrated in environment 1500. In some embodiments, one or more components of FIG. 15 may be the same or similar to one or more other components described herein. In the illustrated embodiment, AW valve assembly 1502 may be the same as AW valve assembly 1402 except with respect to biasing interface 1552 upward and thereby preventing atmospheric valve 1524 from sealing atmospheric channel 1516. Embodiments are not limited in this context.

In the first state a flow from air input channel 1506, into radial air hole 1566-1, and exiting via the atmospheric channel 1516 may create sufficient air pressure between the atmospheric valve 1524 and the atmospheric channel 1516 as to bias the interface 1552 upward and the atmospheric valve 1524 open. In one or more embodiments, a biasing member may include, or refer to, utilization of pressure differentials between different components and/or different portions of a component to bias the components into a configuration.

Transitioning to the second state, the atmospheric valve 1524 may move down to seal the atmospheric channel 1516. In some embodiments, biasing interface 1552 may contact linkage 1556-1 as the second state is entered. Transitioning to the third state, the air input valve 1522 of hat 1522 may move down to seal air input channel 1506 and biasing member 1528-2 may be compressed. Additionally, the primary control valve 1520 may connect the water input channel to the water output channel. Finally, transitioning to the fourth state, biasing member 1528-1 may be compressed and linkage 1556-1 may move down toward hat 1558 to enable the primary control valve 1520 to properly position to connect the water input channel with the balloon channel. In various embodiments, linkage 1556-2 sits on a ledge within the AW valve well 1504. In some embodiments a biasing member may be positioned between the biasing interface 1552 and linkage 1556-1, such as in addition to, or in place of, one or more of biasing members 1528-1, 1528-2.

Figure 16:
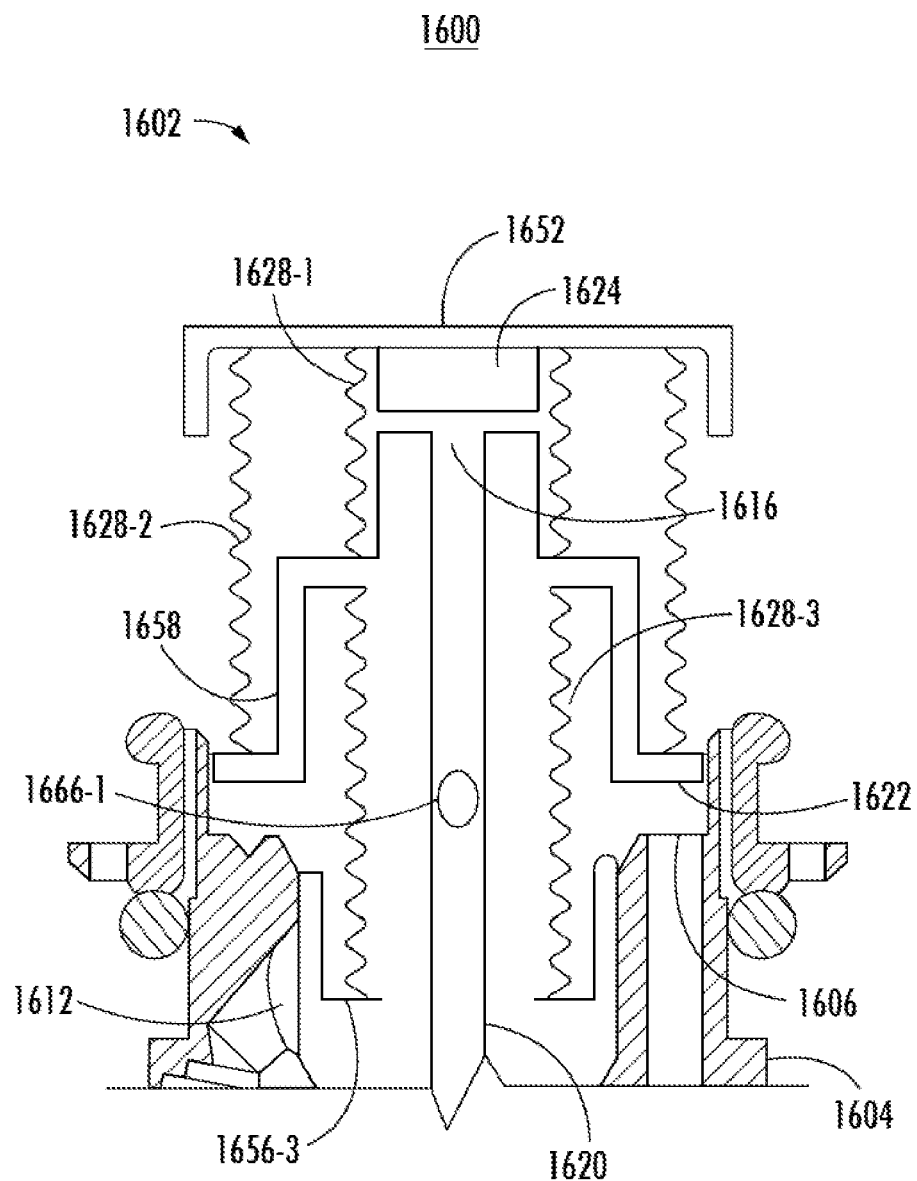
FIG. 16 illustrates various aspects of an exemplary AW valve assembly, according to one or more embodiments described herein.

FIG. 16 illustrates various aspects of an exemplary AW valve assembly 1602 in environment 1600, according to one or more embodiments described herein. In many embodiments, a cross section of one or more portions of AW valve assembly 1602 may be illustrated in environment 1600. In some embodiments, one or more components of FIG. 16 may be the same or similar to one or more other components described herein. In the illustrated embodiment, AW valve assembly 1602 may be the same as AW valve assembly 1402 except with respect to location/characteristics of the biasing members 1628 and configuration/shape of the hat 1658, interface 1652, and linkage 1656-3. Embodiments are not limited in this context.

In many embodiments, the biasing members 1628-1, 1628-2, 1628-3 may be disposed in one or more configurations including concentric, radial, parallel, series, and the like. In AW valve assembly 1602, the hat 1658 may include a first step and a second step. The top of first step may be coupled to interface 1652 with biasing member 1628-2 and the top of the second step may be coupled to interface 1652 with biasing member 1628-1. Further, the bottom of the second step may be coupled to linkage 1656-3 with biasing member 1628-3. In some embodiments, the hat 1658 may include one or more portions of atmospheric channel 1616 and/or primary control valve 1620. In various embodiments, linkage 1656-3 may be inserted into the AW valve well 1604. In some embodiments, linkage 1656-3 may include openings and/or channels to permit flow into air output channel 1610.

In the first state, air may pass from the air input channel 1606 and out of the atmospheric channel 1616. Transitioning to the second state, atmospheric valve 1624 may move down to seal atmospheric channel 1616. During the transition to the second state, biasing members 1628-1, 1628-2 may compress. Transitioning to the third state, biasing member 1628-3 may compress to allow the air input valve 1622 of hat 1658 to seal air input channel 1606. Additionally, the third state may move the primary control valve 1620 and position it to place a water input channel in fluid communication with a water output channel. Transitioning to the fourth state, primary control valve may continue to move down to place a water input channel in fluid communication with a balloon channel.

The medical devices of the present disclosure are not limited, and may include a variety of medical devices for accessing body passageways, including, for example, duodenoscopes, catheters, ureteroscopes, bronchoscopes, colonoscopes, arthroscopes, cystoscopes, hysteroscopes, EUS endoscopes, and the like. In various embodiments, the valve assemblies, or components thereof, described herein may include one or more (e.g., as a single or set of units) of a mounting point, mechanical coupler, bearing, seal, O-ring, actuator, valve, diaphragm, gasket, housing, connector, structural member, manifold, ergonomic features (e.g., finger/thumb grooves, padding, grip, application of mechanical advantage, and the like), spring, bellow, cantilever biasing member, torsional biasing member, linear biasing member, flapper valve, skirt, fin, disc, channel, cavity, lumen, and the like. In many embodiments, one or more components described herein may be constructed utilizing a variety of devices, technologies and/or processes, such as three-dimensional (3D) printing, multi-axis computer numeric control (CNC) machines, additive manufacturing, subtractive manufacturing, injection molding, computer aided design (CAD) programs, path planning programs, machining, forging, casting, and the like.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A medical device, comprising:
 a valve set including a primary control valve, an air input valve, and an atmospheric valve, the primary control valve configured to control flow between a water input channel, a water output channel, and a balloon channel of a valve well, the air input valve configured to control flow through an air input channel of the valve well, and the atmospheric valve configured to control flow through an atmospheric channel;

a valve interface mechanism including a set of biasing members and a user interface mechanism, the set of biasing members comprising first, second, and third biasing members, the user interface mechanism operable between a first state, a second state, a third state, and a fourth state, the first state comprising the valve set configured to place the air input channel in fluid communication with the atmospheric channel, the second state comprising the valve set configured to place the air input channel in fluid communication with an air output channel, the third state comprising the valve set configured to place the water input channel in fluid communication with the water output channel, and the fourth state comprising the valve set configured to place the water input channel in fluid communication with the balloon channel, and wherein the first, second, and third biasing members position the user interface mechanism in the first state when user input is absent.

2. The medical device of claim 1, wherein the first biasing member prevents the atmospheric valve from blocking flow through the atmospheric channel when user input is absent.

3. The medical device of claim 2, wherein the second biasing member prevents the air input valve from blocking flow through the air input channel when user input is absent.

4. The medical device of claim 3, wherein the third biasing member positions the primary control valve to block flow between the water input channel and the water output channel when user input is absent.

5. The medical device of claim 4, wherein the third biasing member positions the primary control valve to block flow between the water input channel and the balloon channel when user input is absent.

6. The medical device of claim 2, the first biasing member comprising a pressure differential between a portion of the atmospheric valve and the atmospheric channel created by configuring the valve set to place the air input channel in fluid communication with the atmospheric channel.

7. The medical device of claim 1, the user interface mechanism comprising an interface, a hat including at least a portion of the air input valve, and one or more linkages, wherein a first linkage is coupled to the primary control valve.

8. The medical device of claim 7, wherein the first biasing member couples the first linkage to the interface.

9. The medical device of claim 8, wherein the second biasing member couples the first linkage to the hat.

10. The medical device of claim 9, wherein the third biasing member couples the hat to a second linkage coupled to the valve well.

11. The medical device of claim 7, the hat comprising at least a portion of the air input valve.

12. The medical device of claim 1, the first biasing member comprising a first bellow and the second biasing member comprising a second bellow, wherein the first and second bellows are disposed in series between the air input valve and the atmospheric channel.

13. The medical device of claim 12, wherein the first and second bellows provide different biasing forces.

14. The medical device of claim 1, wherein the atmospheric valve is biased open due to pressure created by flow from the air input channel.

15. The medical device of claim 1, wherein the valve set includes a flapper valve configured to open due to a pressure buildup when the atmospheric valve blocks flow through the atmospheric channel and the air input valve permits flow through the air input channel.

* * * * *